(12) United States Patent
Ichiki et al.

(10) Patent No.: US 11,123,150 B2
(45) Date of Patent: Sep. 21, 2021

(54) INFORMATION PROCESSING APPARATUS, ASSISTANCE SYSTEM, AND INFORMATION PROCESSING METHOD

(71) Applicant: Sony Corporation, Tokyo (JP)

(72) Inventors: Hiroshi Ichiki, Kanagawa (JP); Takami Mizukura, Kanagawa (JP); Daisuke Tsuru, Chiba (JP); Kentaro Fukazawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/487,097

(22) PCT Filed: Jan. 26, 2018

(86) PCT No.: PCT/JP2018/002449
§ 371 (c)(1),
(2) Date: Aug. 20, 2019

(87) PCT Pub. No.: WO2018/163644
PCT Pub. Date: Sep. 13, 2018

(65) Prior Publication Data
US 2020/0015927 A1 Jan. 16, 2020

(30) Foreign Application Priority Data
Mar. 7, 2017 (JP) .............................. JP2017-042437

(51) Int. Cl.
*A61B 1/002* (2006.01)
*A61B 90/00* (2016.01)
(Continued)

(52) U.S. Cl.
CPC .............. *A61B 90/37* (2016.02); *A61B 1/002* (2013.01); *A61B 1/0661* (2013.01); *A61B 1/273* (2013.01);
(Continued)

(58) Field of Classification Search
CPC . A61B 17/00234; A61B 17/115; A61B 1/002; A61B 1/045; A61B 1/06;
(Continued)

(56) References Cited

U.S. PATENT DOCUMENTS 7,794,396 B2 * 9/2010 Gattani ................. A61B 1/045
600/173
8,331,760 B2 * 12/2012 Butcher ......... H04N 21/234318
382/256
(Continued)

FOREIGN PATENT DOCUMENTS

| CN | 101179711 A | 5/2008 |
| CN | 103460214 A | 12/2013 |

(Continued)

OTHER PUBLICATIONS

International Search Report and Written Opinion dated Apr. 24, 2018 for PCT/JP2018/002449 filed on Jan. 26, 2018, 13 pages including English Translation of the International Search Report.

*Primary Examiner* — Thai Q Tran
*Assistant Examiner* — Stephen R Smith
(74) *Attorney, Agent, or Firm* — Xsensus LLP

(57) ABSTRACT

[Object] To provide an information processing apparatus, an assistance system, and an information processing method that enable suitable assistance to be performed on a surgeon. [Solving Means] An information processing apparatus includes a control unit. The control unit extracts, on the basis of a first image obtained by picking up an image of a surgical part including an affected part and metadata of a situation obtained from past surgery or examination, a parameter of assistance performed with respect to the situation, which is made to correspond to the metadata.

11 Claims, 21 Drawing Sheets

(51) Int. Cl.
*G16H 20/40* (2018.01)
*G16H 30/20* (2018.01)
*A61B 1/06* (2006.01)
*A61B 1/273* (2006.01)
*A61B 1/31* (2006.01)
*A61B 5/02* (2006.01)
*A61B 17/00* (2006.01)
*A61B 17/115* (2006.01)
*G06K 9/20* (2006.01)
*H04N 5/235* (2006.01)
*H04N 5/225* (2006.01)

(52) U.S. Cl.
CPC ............ *A61B 1/31* (2013.01); *A61B 5/02042* (2013.01); *A61B 17/00234* (2013.01); *A61B 17/115* (2013.01); *G06K 9/2027* (2013.01); *G16H 20/40* (2018.01); *G16H 30/20* (2018.01); *H04N 5/2354* (2013.01); *A61B 2090/373* (2016.02); *G06K 2209/27* (2013.01); *H04N 2005/2255* (2013.01)

(58) Field of Classification Search
CPC ......... A61B 1/0661; A61B 1/273; A61B 1/31; A61B 2090/373; A61B 34/10; A61B 5/02042; A61B 90/37; G02B 23/24; G02B 23/26; G06K 2209/057; G06K 2209/27; G06K 9/00624; G06K 9/2027; G06T 1/00; G09G 5/00; G09G 5/02; G16H 20/40; G16H 30/20; H04N 2005/2255; H04N 5/225; H04N 5/2354
USPC ................ 348/68, 65, 71, 77; 382/128, 132
See application file for complete search history.

(56) References Cited

U.S. PATENT DOCUMENTS

| | | | |
|---|---|---|---|
| 9,547,940 B1* | 1/2017 | Sun | A61B 1/00147 |
| 9,824,189 B2* | 11/2017 | Sawada | G06F 19/3418 |
| 9,900,503 B1* | 2/2018 | Bedi | H04N 9/646 |
| 9,972,093 B2* | 5/2018 | Zhao | G06T 7/12 |
| 9,996,922 B2* | 6/2018 | Gazit | G06T 7/11 |
| 9,996,935 B2* | 6/2018 | Srinivasan | G06T 7/0012 |
| 10,292,684 B2* | 5/2019 | Okazaki | A61B 8/0883 |
| 10,345,582 B2* | 7/2019 | Schneider | A61B 90/30 |
| 10,521,904 B2* | 12/2019 | Teramura | G06T 7/0012 |
| 10,614,555 B2* | 4/2020 | Fukazawa | G06T 7/70 |
| 10,650,267 B2* | 5/2020 | Yoshida | G06F 19/321 |
| 2008/0108873 A1 | 5/2008 | Gattani et al. | |
| 2009/0245600 A1* | 10/2009 | Hoffman | H04N 13/156 382/128 |
| 2015/0339817 A1* | 11/2015 | Kuriyama | G06T 7/64 348/71 |

FOREIGN PATENT DOCUMENTS

| | | |
|---|---|---|
| JP | 2005-110878 A | 4/2005 |
| JP | 2007-181670 A | 7/2007 |
| JP | 2009-77765 A | 4/2009 |
| JP | 2011-505225 A | 2/2011 |
| JP | 2011-87962 A | 5/2011 |
| JP | 2012-152279 | 8/2012 |
| JP | 2012-152332 A | 8/2012 |
| JP | 2014-35703 A | 2/2014 |
| JP | 2014-505950 A | 3/2014 |
| JP | 2015-507951 A | 3/2015 |
| JP | 2015-146864 A | 8/2015 |
| JP | 2015-527100 A | 9/2015 |
| JP | 2016-7444 A | 1/2016 |
| JP | 2016-513540 A | 5/2016 |
| JP | 2016-158752 A | 9/2016 |
| JP | 2016-525905 A | 9/2016 |
| JP | 2016-533199 A | 10/2016 |
| JP | 2016-534811 A | 11/2016 |
| JP | 2017-33189 A | 2/2017 |
| JP | 2017-504019 A | 2/2017 |
| WO | 2015/064435 A | 5/2015 |

* cited by examiner

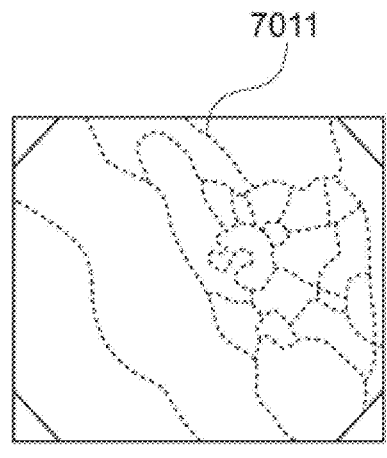
(a)
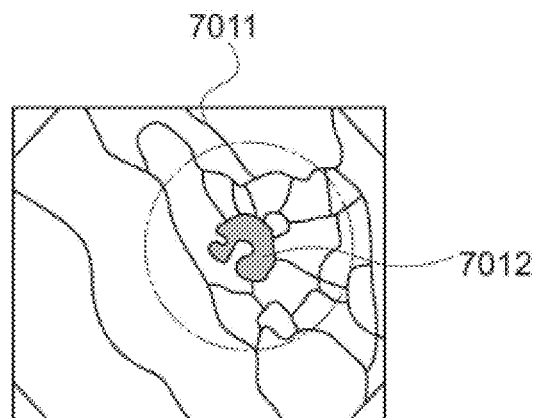
(b)
FIG.20

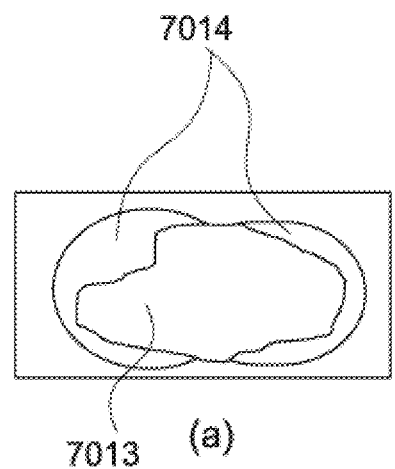
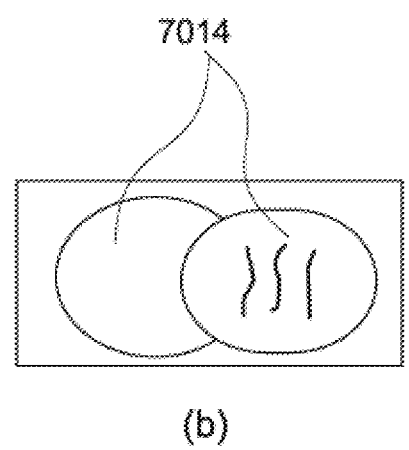
FIG.22

INFORMATION PROCESSING APPARATUS, ASSISTANCE SYSTEM, AND INFORMATION PROCESSING METHOD

CROSS-REFERENCE TO RELATED APPLICATIONS

The present application is based on PCT filing PCT/JP2018/002449, filed Jan. 26, 2018, which claims priority to JP 2017-042437, filed Mar. 7, 2017, the entire contents of each are incorporated herein by reference.

TECHNICAL FIELD

The present technology relates to an information processing apparatus, an assistance system, and an information processing method to be used for assistance in surgery and the like.

BACKGROUND ART

There has been proposed an assistance system capable of performing suitable assistance by causing a monitor to display a live image of surgery and an image relevant thereto during operation (e.g., see Patent Literature 1). This assistance system is configured such that an examination image relevant to a patient and a surgical image relevant to a surgical procedure as well as the live image can be displayed on the monitor.

CITATION LIST

Patent Literature

Patent Literature 1: Japanese Patent Application Laid-open No. 2005-110878

DISCLOSURE OF INVENTION

Technical Problem

However, in such an assistance system, relevant information such as the surgical image relevant to the surgical procedure is displayed on the monitor while a surgeon needs to correctly recognize multiple pieces of relevant image information and determine relevant image information suitable for a situation at that time from among them.

It is an object of the present technology to provide an information processing apparatus, an assistance system, and an information processing method that enable suitable assistance depending on a situation to be automatically performed on a surgeon.

Solution to Problem

An information processing apparatus according to an embodiment of the present technology includes a control unit.

The control unit extracts, on the basis of a first image obtained by picking up an image of a surgical part including an affected part and metadata of a situation obtained from past surgery or examination, a parameter of assistance performed with respect to the situation, which is made to correspond to the metadata.

In accordance with this embodiment, suitable assistance depending on the situation shown in that first image is automatically performed on the basis of the first image, and thus the surgeon can perform more suitable surgery and the like.

The control unit may calculate the metadata similar to an image recognition result of the first image and extracts the parameter made to correspond to the calculated metadata.

With this configuration, the assistance according to the parameter made to correspond to the metadata similar to the situation shown in the first image is performed.

The control unit may change an image pickup condition of the surgical part on the basis of the extracted parameter.

As described above, assistance to provide an image pickup condition suitable according to the situation shown in the first image can be performed.

The control unit may change the image pickup condition by changing irradiation light with which the surgical part is to be irradiated, on the basis of the extracted parameter.

As described above, the change in image pickup condition may be changing the irradiation light with which the surgical part is to be irradiated. For example, an image picked up using narrow band light as the irradiation light is an image in which a superficial blood vessel is emphasized and observation of the affected part can be more correctly performed. Further, an image picked up using special light for transmission through blood as the irradiation light in a situation where it is difficult to determine a tissue due to a large amount of bleeding is an image from which a blood portion is removed, and it becomes easy to determine the tissue.

The control unit may change the image pickup condition by adjusting a scale and a focal point at a time of image pickup on the basis of the extracted parameter.

As described above, the change in image pickup condition may be adjustment of the scale and the focal point at the time of image pickup. With this configuration, for example, the affected part displayed in an enlarged state can be observed.

The control unit may cause a display apparatus to display a second image obtained by changing the image pickup condition on the basis of the extracted parameter and picking up an image of the surgical part.

With this configuration, the surgeon more suitable surgery and the like can perform while viewing the second image displayed on the display apparatus.

The control unit may cause a display apparatus to display a second image whose image quality is adjusted by causing the first image to be subjected to image processing on the basis of the extracted parameter.

The surgical part may include a first tissue and a second tissue, and the control unit may cause the display apparatus to display the second image whose image quality is adjusted by causing the first image to be subjected to image processing such that a hue difference between the first tissue and the second tissue in the first image on the basis of the extracted parameter.

With this configuration, the second image whose image quality is adjusted can be obtained in such a manner that the first tissue in the surgical part is emphasized, and the surgeon can correctly grasp a region in which the first tissue is present.

The control unit may cause a display apparatus to display a past image or video to be a reference on the basis of the extracted parameter.

As described above, in such a manner that an image or video to be a reference, which is generated in the past under a situation similar to the situation shown in the first image is displayed, the surgeon can predict danger and can perform more suitable surgery.

The control unit may extract, if determining that the first image has a situation of low visibility on the basis of the first image and the metadata, the parameter to cause the display apparatus to display an image picked up before the low visibility is caused. With this configuration, for example, the image picked up before the low visibility is caused can be checked even if the low visibility is caused by smoke and the like generated when cutting the affected part with a radio knife, and the field of view of the surgeon can be ensured.

The control unit may cause assistance information to be reported on the basis of the extracted parameter.

For example, in a case where the situation shown in the first image is similar to a situation at a time of failure of anastomosis using a stapler in the past, the assistance information of warning for urging to pay attention can be reported to the surgeon. As the reporting method, a text of the warning for urging the user to pay attention may be displayed on the display apparatus or may be reported as sound.

An assistance system according to the embodiment of the present technology includes a database of metadata, a database of a parameter, and a control unit.

In the database of metadata, metadata of a situation obtained from past surgery or examination is stored.

In the database of a parameter, a parameter of assistance performed with respect to the situation made to correspond to the metadata is stored.

The control unit calculates, on the basis of the database of the metadata, metadata similar to an image recognition result of a first image obtained by picking up an image of a surgical part including an affected part and extracts the parameter made to correspond to the calculated metadata.

In accordance with this embodiment, the assistance according to the parameter made to correspond to the metadata similar to the situation shown in the first image is automatically performed, and the surgeon can perform more suitable surgery and the like.

An information processing method according to the embodiment of the present technology includes acquiring an image recognition result of a first image, calculating metadata, and extracting a parameter.

The acquisition of the image recognition result of the first image is performed by acquiring an image recognition result of a first image obtained by picking up an image of a surgical part including an affected part.

The calculation of the metadata is performed by calculating metadata similar to the image recognition result of the first image from a database of metadata in which metadata of a situation obtained from past surgery or examination is stored.

The extraction of the parameter is performed by extracting a parameter of assistance performed with respect to the situation, which is made to correspond to the calculated metadata.

In accordance with this embodiment, the assistance according to the parameter made to correspond to the metadata similar to the situation shown in the first image is automatically performed, and the surgeon can perform more suitable surgery and the like.

Advantageous Effects of Invention

As described above, in accordance with the present technology, suitable assistance can be automatically performed on a surgeon.

It should be noted that the effects described here are not necessarily limitative and any effect described in the present disclosure may be provided.

BRIEF DESCRIPTION OF DRAWINGS

FIG. 20 A view depicting images of a surgical part before and after image quality adjustment in the assistance system according to the seventh embodiment.

FIG. 22 A view depicting images of a surgical part before and after irradiation light switching in the assistance system according to the eighth embodiment.

MODE(S) FOR CARRYING OUT THE INVENTION

Hereinafter, an embodiment according to the present technology will be described with reference to the drawings. In the embodiment below, an assistance system applied to an endoscopic surgery system will be mainly described. Hereinafter, the example in which it is applied to the endoscopic surgery system will be mainly described, though it can also be applied to an endoscopic examination system that examines and diagnoses the state of a target organ.

[Outline of Assistance System]

In the assistance system according to this embodiment, an image to be assistance for a surgeon which is suitable for a situation of surgery is configured to be displayed on a display apparatus. In the assistance system, assistance depending on that situation is automatically performed on the basis of a first image which is a live image obtained by picking up an image of a surgical part including a site which is a surgery target or an examination target. As the specific assistance, there are adjustment of a scale and a focal point of a picked up image, switching of an irradiation light source, display of a second image in which an affected part (lesion site) is emphasized, display of a second image in which an affected part is displayed in an enlarged state, reporting advice or a possible danger, display of video or an image of a case which occurred under a similar situation in the past, display of a previous image when low visibility is caused, and the like.

With this configuration, the surgeon can obtain an image and the like suitable for the situation of the surgery without taking the trouble to perform processes including adjustment of a scale and a focal point of a picked up image and switching of an illumination light source during the surgery. Further, by receiving assistance to report advice or a possible danger and receiving assistance of display of a past case, the surgeon can notice a point not noticed and can perform more suitable surgery. Further, for example, a poor experienced surgeon can perform more suitable surgery on the basis of the assistance performed by the assistance system even if an experienced doctor is absent in that place.

Conventionally, even with a high-functioning assistance system, an operator has needed to be familiar with the system and perform an operation depending on a situation in order to make full use of the functions. In contrast, in the assistance system of this embodiment, assistance of emphasized image display and the like suitable for that situation is automatically performed on the basis of the first image which is the live image, and it is thus unnecessary to perform a complicated operation and the like for displaying an image depending on a surgery situation.

Figure 1:
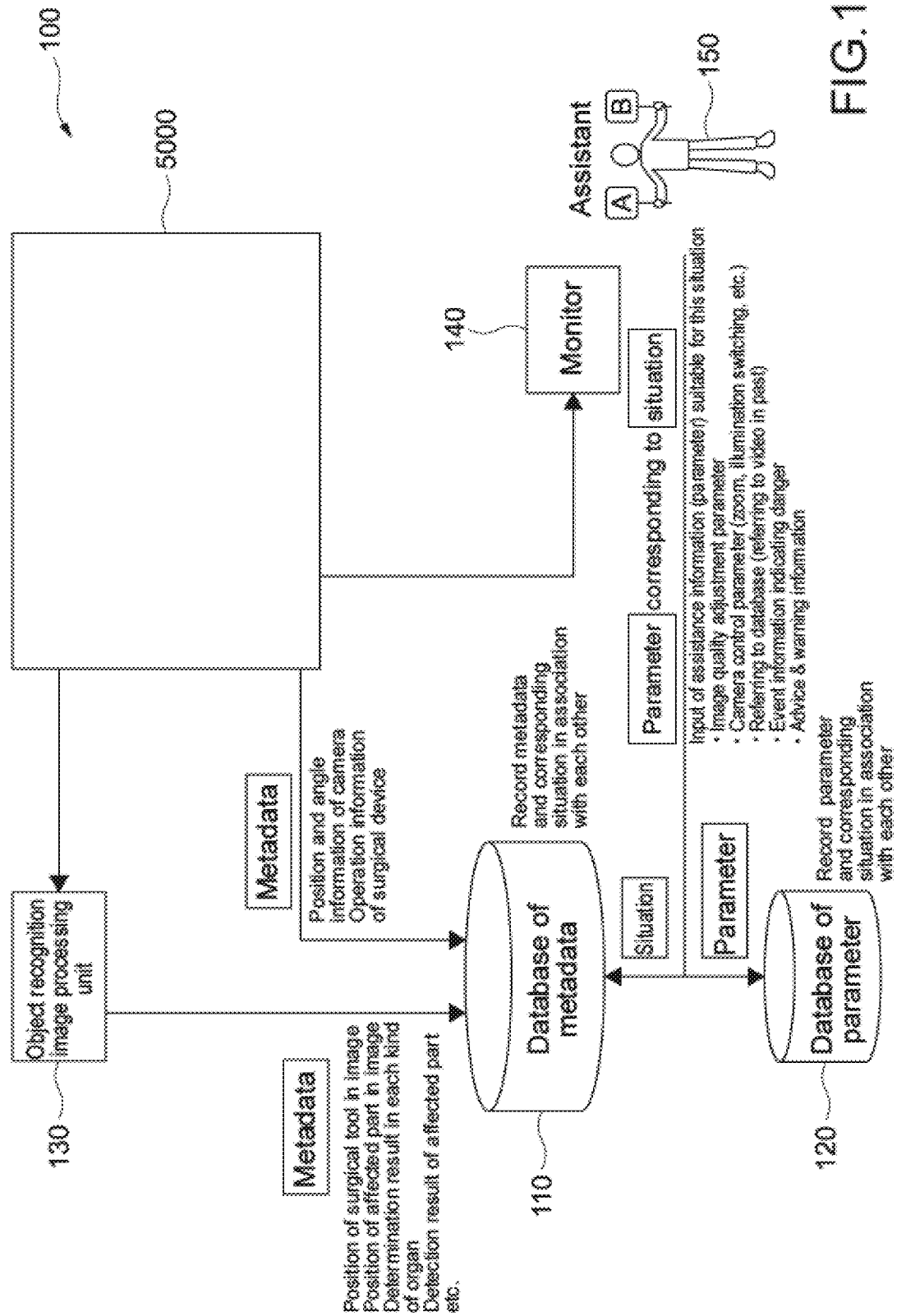
FIG. 1 A schematic diagram depicting a configuration of an assistance system at a time of generation of a database according to the present technology.
Figure 2:
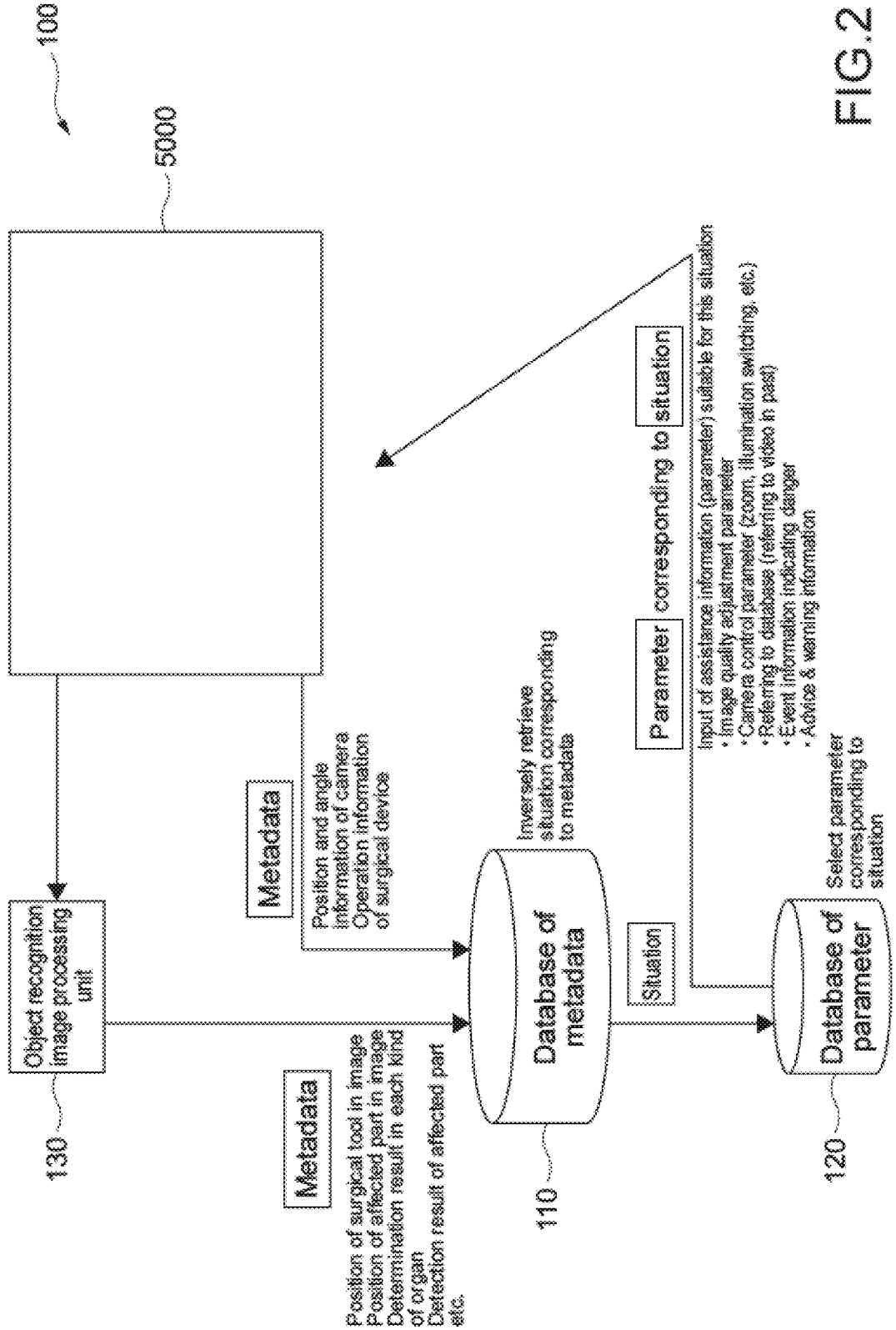
FIG. 2 A schematic diagram depicting a configuration of the assistance system at a time of use of the database according to the present technology.
Figure 3:
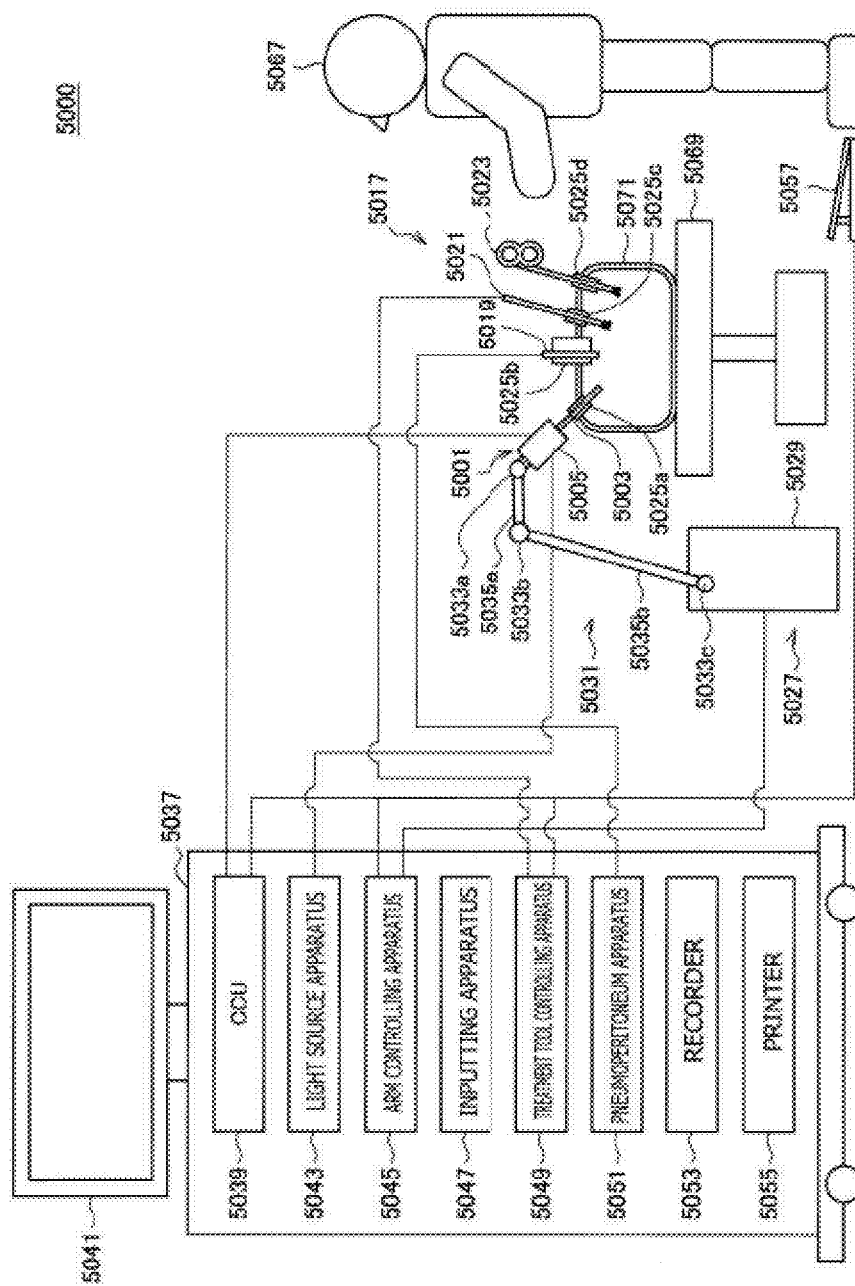
FIG. 3 A view depicting an example of a schematic configuration of an endoscopic surgery system that constitutes a part of the assistance system.
Figure 4:
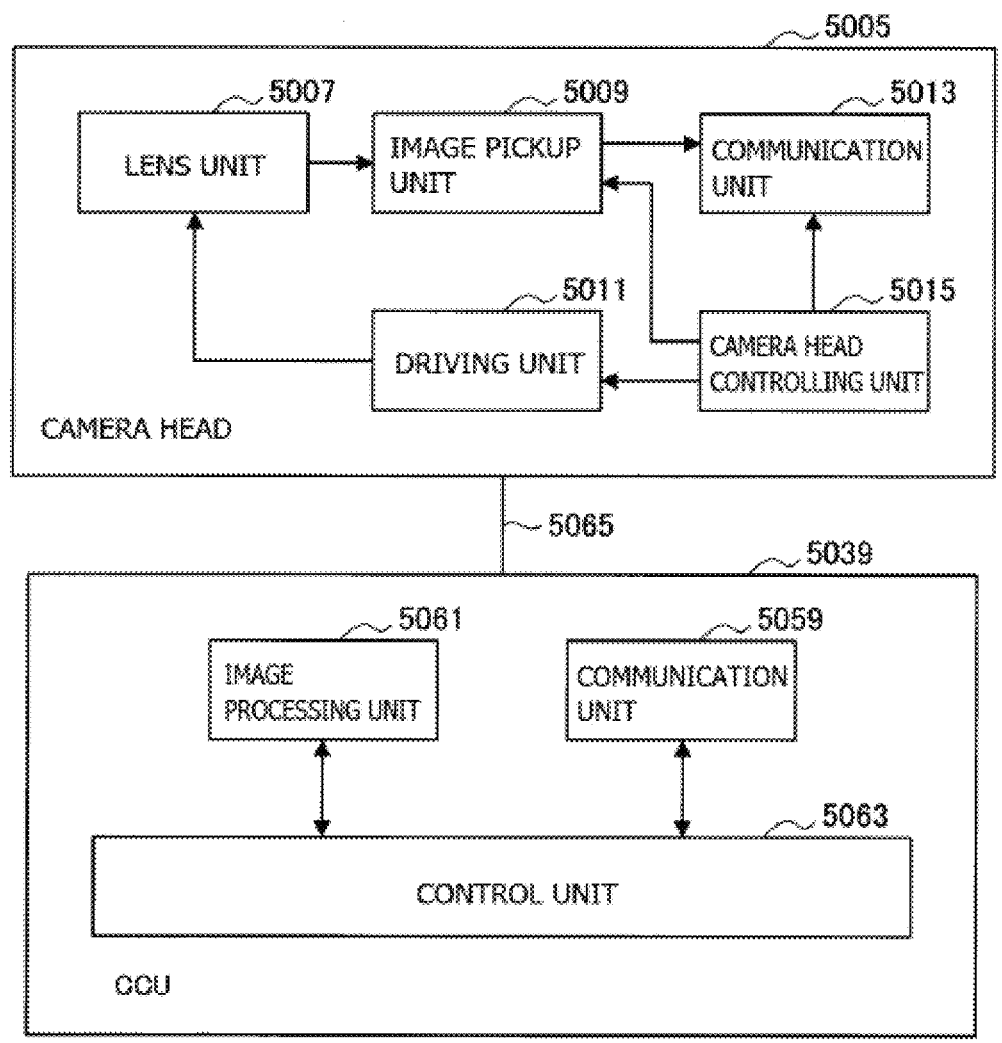
FIG. 4 A block diagram depicting an example of a functional configuration of a camera head and a camera control unit (CCU) depicted in FIG. 3.

FIGS. 1 and 2 are schematic diagrams depicting a configuration of an assistance system 100. FIG. 1 depicts a configuration of the assistance system 100 at a time of generation of a database. FIG. 2 depicts a configuration of the assistance system 100 at a time of use of the database. FIG. 3 is a schematic diagram depicting a configuration of an endoscopic surgery system 5000 that constitutes a part of the assistance system 100. FIG. 4 is a block diagram depicting an example of functional configurations of a camera head and a CCU depicted in FIG. 3. It should be noted that details of configurations of the assistance system 100 at the time of generation and use of the database will be described later.

The assistance system 100 includes a database 110 of metadata in which the metadata is stored, a database 120 of parameters in which the parameters made to correspond to the metadata stored in the database 110 of metadata are stored, a control unit 5063, and an object recognition image processing unit 130.

In the database 110 of metadata, metadata of situations obtained from past surgery results and examination results are stored in advance. In the database 120 of parameters, assistance performed with respect to that metadata (situation) is stored as parameters in advance while being made to correspond to the metadata.

In the database 110 of metadata, metadata of a situation associated with an image and metadata of a situation associated with an apparatus are stored.

The metadata of the situation associated with the image includes the kind of surgical procedure, a purpose (operative surgical procedure), the presence and absence of a surgical tool, the position of the surgical tool in an image, the position of an affected part in the image which is a surgery target site, the kind of target affected part (organ to which attention should be paid), the kind of affected part (situation of the surgical procedure), and the like. In addition, it includes a detection result of the surgical part including the affected part, for example, color components (R, G, B) of the surgical part, image gradient information, a texture pattern, and the like, for example. The metadata of the situation associated with the image is generated on the basis of an image recognition result of recognition by the object recognition image processing unit 130 using an object recognition technique in the field of image processing.

The metadata of the situation associated with the apparatus includes position and angle information of a camera that picks up an image of the surgical part, the kind of light source of irradiation light, operation information of a surgical device, and the like, for example.

Multiple pieces of metadata of the situation associated with the image and multiple pieces of metadata of the situation associated with the apparatus are made to correspond to one image (situation).

Here, the kind of surgical procedure includes, for example, a stomach cancer, a stomach polyp, a foreign matter in a stomach, an ureteral calculus, bleeding of an alimentary canal, and the like and indicates the kinds of target organ and affected part and the like. Further, the purpose (operative surgical procedure) includes, for example, polypectomy, mucosal resection, submucosal dissection, stent placement, hemostasis, incision, lithotripsy and excision for a calculus and the like, papillary balloon dilation, drainage, excision of a foreign matter and the like, examination, and the like. The target affected part (organ to which attention should be paid) includes, for example, a pylorus, a body of stomach, a cardia, an ascending colon, a transverse colon, a descending colon, a sigmoid colon, a rectum, and the like and indicates the position of an affected part in the target organ. The kind of affected part (situation of the surgical procedure) includes, for example, an adenomatous polyp, a hyperplastic polyp, a fundic gland polyp, an inflammatory polyp, a cancer, a foreign matter, inflammation, a calculus, bleeding, and the like.

The parameter includes an image-quality adjustment parameter, a camera control parameter for changing an image pickup condition by controlling an operation and the like of the camera head such as switching of irradiation light of the camera and adjustment of a scale and a focal point of a picked up image, a parameter of past video for referring to the past video, a parameter of event information indicating a danger, a parameter for reporting advice, warning, and the like, and the like.

[Endoscopic Surgery System]

Next, the endoscopic surgery system 5000 will be described.

FIG. 3 is a view depicting an example of a schematic configuration of an endoscopic surgery system 5000 to which the technology according to an embodiment of the present disclosure can be applied. In FIG. 3, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body cavity of the patient 5071 through the trocars 5025a to 5025d. In the example depicted, as the other surgical tools 5017, a pneumoperitoneum tube 5019, an energy device 5021 and forceps 5023 are inserted into body cavity of the patient 5071. Further, the energy device 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, tweezers or a retractor may be used.

An image of a surgical region in a body cavity of the patient 5071 imaged by the endoscope 5001 is displayed on a display apparatus 5041. The surgeon 5067 would use the energy device 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy device 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body cavity of the patient 5071, and a camera head 5005 connected to a proximal end of the lens barrel 5003. In the example depicted, the endoscope 5001 is depicted as a rigid endoscope having the lens barrel 5003 of the hard type. However, the endoscope 5001 may otherwise be configured as a flexible endoscope having the lens barrel 5003 of the flexible type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body cavity of the patient 5071 through the objective lens. It is to be noted that the endoscope 5001 may be a forward-viewing endoscope or may be an oblique-viewing endoscope or a side-viewing endoscope.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy device 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy device 5021 for cautery or incision of a tissue, sealing of a blood vessel or the like. A pneumoperitoneum apparatus 5051 feeds gas into a body cavity of the patient 5071 through the pneumoperitoneum tube 5019 to inflate the body cavity in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033a, 5033b and 5033c and the plurality of links 5035a and 5035b connected to each other by the joint portion 5033b. In FIG. 3, for simplified illustration, the configuration of the arm unit 5031 is depicted in a simplified form. Actually, the shape, number and arrangement of the joint portions 5033a to 5033c and the links 5035a and 5035b and the direction and so forth of axes of rotation of the joint portions 5033a to 5033c can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body cavity of the patient 5071.

An actuator is provided in each of the joint portions 5033a to 5033c, and the joint portions 5033a to 5033c are configured such that they are rotatable around predetermined axes of rotation thereof by driving of the respective actuators. The driving of the actuators is controlled by the arm controlling apparatus 5045 to control the rotational angle of each of the joint portions 5033a to 5033c thereby to control driving of the arm unit 5031. Consequently, control of the position and the posture of the endoscope 5001 can be implemented. Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the operating room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colors can be picked up time-divisionally. According to the method just described, a color image can be obtained even if a color filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower wavelength band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrow-band light and/or excitation light suitable for special light observation as described above.

(Camera Head and CCU)

Functions of the camera head 5005 of the endoscope 5001 and the CCU 5039 are described in more detail with reference to FIG. 4. FIG. 4 is a block diagram depicting an example of a functional configuration of the camera head 5005 and the CCU 5039 depicted in FIG. 3.

Referring to FIG. 4, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in color. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated. The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy device 5021 is used and so forth by detecting the shape, color and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the operating room. Therefore, such a situation that movement of medical staff in the operating room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a flexible endoscopic system for inspection or a microscopic surgery system.

Figure 5:
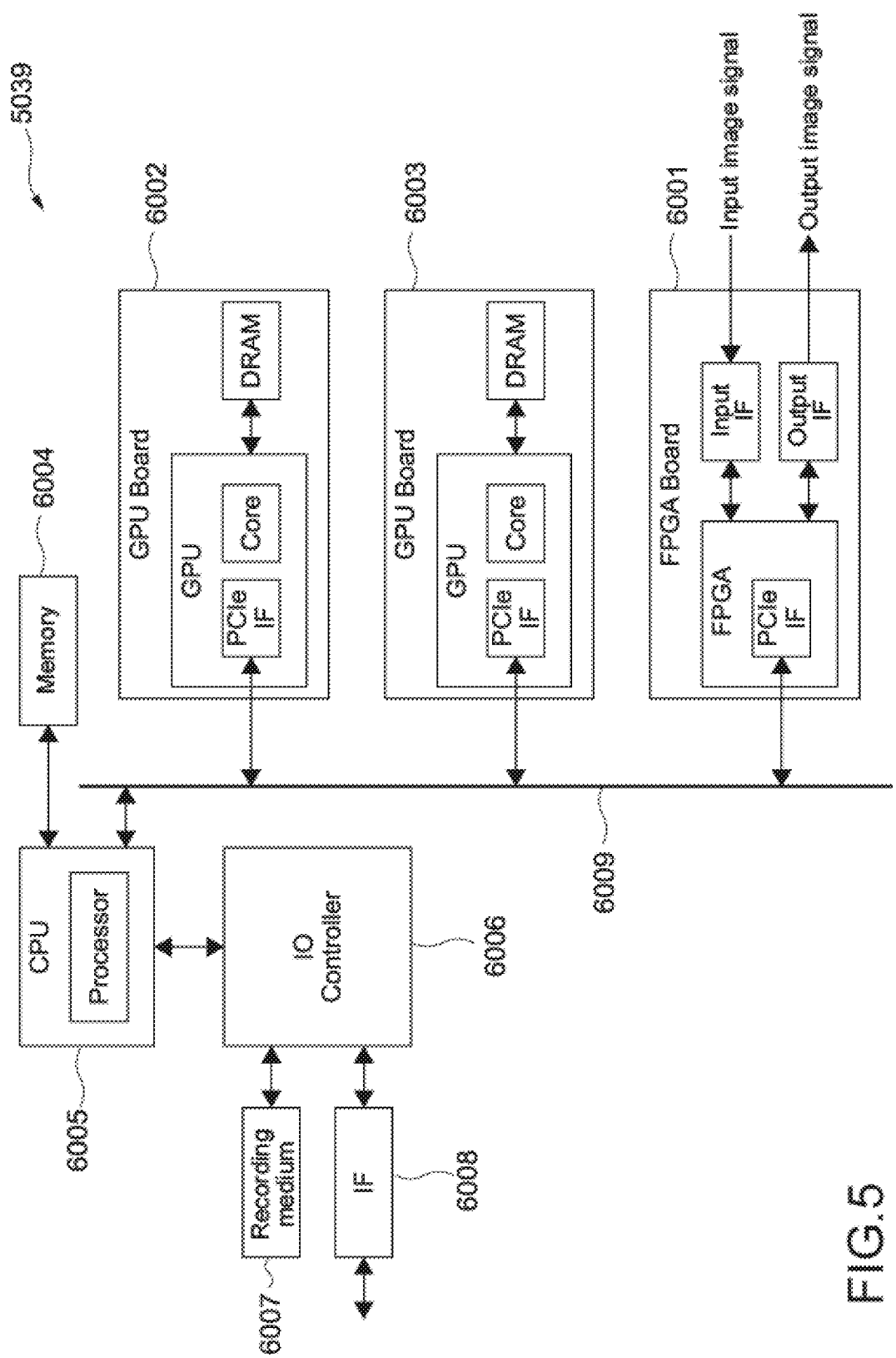
FIG. 5 An explanatory diagram depicting an example of the hardware configuration of the CCU shown in FIG. 3.

FIG. 5 is an explanatory diagram depicting an example of a hardware configuration of the CCU 5039 in FIG. 3. The CCU 5039 includes, for example, a field-programmable gate array (FPGA) board 6001, a CPU 6005, GPU boards 6002 and 6003, a memory 6004, an IO controller 6006, a recording medium 6007, and an interface 6008. Further, the FPGA board 6001, the CPU 6005, and the GPU boards 6002 and 6003 are connected via a bus 6009, for example. The FPGA board 6001 includes, for example, an FPGA, an input interface via which an input image signal is input from the endoscope 5001 of FIG. 3, and an output interface via which an output image signal is output to the display apparatus 5041 of FIG. 3.

The CPU 6005 and the GPU boards 6002 and 6003 execute various types of software such as relevant software, for example, for performing various types of processing. The CPU 6005 includes a processor. Each of the GPU boards 6002 and 6003 includes a graphics processing unit (GPU) and a dynamic random access memory (DRAM).

In the memory 6004, various types of data, for example, data corresponding to an input image signal from the endoscope 5001, data corresponding to an output image signal to the display apparatus 5041, and the like are stored. The CPU 6005 serves to control writing and reading of various types of data in and from the memory 6004.

The CPU 6005 divides image data stored in the memory 6004 in accordance with data stored in the memory 6004, processing capability of the GPU boards 6002 and 6003, and processing contents. Then, each GPU of the GPU boards 6002 and 6003 subjects the divided and supplied data to predetermined processing and outputs a result of the processing to the CPU 6005.

The IO controller 6006 serves to control transfer of a signal between the CPU 6005 and the recording medium 6007 and the interface 6008, for example.

The recording medium 6007 functions as a storage unit (not depicted) and stores various types of data such as image data and various applications. Here, examples of the recording medium 6007 can include a solid-state drive and the like. Further, the recording medium 6007 may be removable from the CCU 5039.

Examples of the interface 6008 can include a universal serial bus (USB) terminal and a processing circuit, a local area network (LAN) terminal and a transmission and reception circuit, and the like.

It should be noted that the hardware configuration of the CCU 5039 is not limited to the configuration depicted in FIG. 5. For example, FIG. 5 depicts an example in which two GPU boards, the GPU boards 6002 and 6003, are provided. However, two or more GPU boards may be provided. Further, in a case where the CPU 6005 has a GPU function, the CCU 5039 does not need to include the GPU boards 6002 and 6003.

The assistance system according to the present disclosure is favorably applied to an endoscopic surgery system and an endoscopic examination system. By applying the technology according to the present disclosure to the endoscopic surgery system, an image suitable for a situation of surgery can be obtained. Therefore, the surgery can be performed more safely and more suitably. Further, a more certain diagnosis can be performed by applying the technology according to the present disclosure to the endoscopic examination system.

[Configuration of Assistance System at Time of Database Generation]

The description will be made with reference to FIGS. 1, 3, and 4. FIG. 1 is a schematic diagram depicting a configuration of the assistance system 100 at the time of generation of the database. Here, a case where the respective databases of metadata and parameters are generated will be described.

As depicted in FIG. 1, the assistance system 100 at the time of generation of the database includes the endoscopic surgery system 5000, the object recognition image processing unit 130, the database 110 of metadata, the database 120 of parameters, and a monitor 140.

FIG. 3 depicts a state in which the surgeon (medical doctor) 5067 is performing surgery on the patient 5071 on the patient bed 5069 by using the endoscopic surgery system 5000. As depicted in the figure, the endoscopic surgery system 5000 includes the endoscope 5001, the other surgical tools 5017, the supporting arm apparatus 5027 that supports the endoscope 5001, and the cart 5037 on which various apparatuses for endoscopic surgery are mounted. The display apparatus 5041, the CCU 5039, and the like are mounted on the cart 5037. As depicted in FIG. 4, the CCU 5039 is an information processing apparatus including the control unit 5063, the communication unit 5059, and the image processing unit 5061.

In the assistance system 100 at the time of generation of the database, the first image picked up by the endoscope 5001 is displayed on the display apparatus 5041 and the same image as the image displayed on the display apparatus 5041 is displayed on the monitor 140. The monitor 140 is placed in a room different from the surgical room and an assistant (a medical specialist, an experienced doctor, or the like) 150 can check display of the monitor 140. Further, an image pickup condition and the like of the surgical part are configured to be capable of being changed by the assistant 150.

In the assistance system 100 at the time of generation of the database, the assistant 150 observes a state in which the surgeon (medical doctor) 5067 is performing surgery on the patient by using the endoscopic surgery system 5000 through the monitor 140 and performs assistance suitable for that situation. In this manner, a database is generated.

While viewing the first image displayed on the monitor 140, the assistant 150 performs assistance to change an image pickup condition such as adjustment of a scale and a focal point and switching of irradiation light so as to provide image display suitable for that surgery situation. The second image picked up and acquired on the basis of the assistance performed by the assistant 150 is displayed on the display apparatus 5041. Further, the assistant 150 performs assistance and the like to cause the display apparatus 5041 to display advice or warning suitable for that surgery situation for reporting it.

In the assistance system 100 at the time of generation of the database, the control unit 5063 generates metadata of the situation on the basis of an image recognition result of the first image recognized by the object recognition image processing unit 130 and stores it in the database 110 of metadata. Then, the control unit 5063 stores the parameter of the assistance by the assistant 150 with respect to that situation in the database 120 of parameters while being made to correspond to this metadata (situation).

In the database 110 of metadata, stored are metadata of the kind of surgical procedure, a purpose, the position of a surgical tool in an image, the position of an affected part in the image which is a surgery target site, the kind of target affected part (organ to which attention should be paid), the kind of affected part (lesion site), and the like, metadata of the situation associated with the image, for example, metadata of a detection result of the surgical part including the affected part and the like, for example, color components (R, G, B) of the surgical part, image gradient information, a texture pattern, and the like, and metadata of the situation associated with the apparatus, for example, position and angle information of a camera that picks up an image of the surgical part, the kind of light source of irradiation light, operation information of a surgical device, and the like.

The metadata of the situation associated with the image is generated on the basis of an image recognition result of recognition by the object recognition image processing unit 130. The object recognition image processing unit 130 retains information indicating characteristics of an object, for example, an affected part, a surgical tool, or the like in advance and extracts and recognizes the characteristics retained in advance from the image (first image) of the surgical part including the surgery target site, which is picked up by the image pickup unit 5009 provided in the camera head 5005. The object recognition by the object recognition image processing unit 130 can be performed using a known object recognition technique in the field of image processing.

In the database 120 of parameters, stored are an image-quality adjustment parameter, a camera control parameter for controlling an operation and the like of the camera head, such as switching of irradiation light of the camera, and adjustment of the scale and the focal point, and the like, a parameter of display of past video for referring to the past video, a parameter of event information display indicating danger, a parameter for reporting advice, warning, and the like, which are made to correspond to the metadata (situation).

The control unit 5063 generates metadata on the basis of an image recognition result of the recognition by the object recognition image processing unit 130 and stores it in the database 110 of metadata. Then, the control unit 5063 stores, in the database 120 of parameters, assistance performed by the assistant 150 with respect to the situation (metadata) as a parameter while making it correspond to that metadata.

Here, the description will be made by exemplifying a case where the image displayed on the monitor 140 is the polyp of the colon and the assistant 150 performs adjustment of the scale and the focal point of the camera and a change in image pickup condition, that is, changing the kind of irradiation light with which the surgical part is irradiated into special light so as to provide the enlarged display of the polyp of the colon and an image of observation with the special light.

In such a case, the situation such as the position of the affected part, the color components (R, G, B) of the surgical part, the image gradient information, and the texture pattern are subjected to image recognition by the object recognition image processing unit 130. The control unit 5063 generates metadata on the basis of this image recognition result, the kind of surgical procedure (here, the colon polyp), and the like which are input by the surgeon in advance and stores it in the database 110 of metadata. Then, the control unit 5063 changes the image pickup condition (control on the camera) made by the assistant 150 while making it correspond to this metadata and stores, in the database 120 of parameters, a parameter to display the second image acquired by picking up an image under this changed image pickup condition. In this manner, the databases of metadata and parameters are generated.

It should be noted that although the example in which the assistance is performed by the assistant 150 other than the surgeon 5067 has been shown in this embodiment, in a case where the surgeon 5067 himself/herself is an experienced doctor, the surgeon 5067 himself/herself may generate, as the assistant, a database by setting an operation and the like performed by the surgeon 5067 as the parameter. Further, although the description has been made by exemplifying the surgery here, it can also be applied to examination. For example, the experienced doctor may perform examination and generate a database by setting a situation shown in the first image as the metadata and setting an operation performed by the doctor with respect to this metadata as the parameter.

Further, the example in which the assistant observes the surgery in real time, performs the assistance, and generates the database has been shown here, though not limited thereto. For example, the assistant may propose assistance depending on that surgery situation and generate a database while watching video of the surgery which has already been performed by the surgeon. The assistance includes display of an image or video in a dangerous event generated in the past similar situation, display of an image or video of surgery in the past similar situation, and the like as well as switching the irradiation light, camera control such as adjustment of the scale and focal point, and reporting advice, warning, and the like as described above.

[Assistance System at Time of Use of Database]

Next, a case of utilizing the assistance system 100 configured in the above-mentioned manner will be described. FIG. 2 is a schematic diagram depicting a configuration of the assistance system 100 at the time of use of the database. Configurations similar to those described above will be denoted by similar reference signs and the descriptions will be omitted in some cases.

As depicted in FIG. 2, the assistance system 100 at the time of use of the database includes the endoscopic surgery system 5000, the object recognition image processing unit 130, the database 110 of metadata, and the database 120 of parameters. In this embodiment, even without receiving assistance of advice about an image quality adjustment operation of the image and the like, for example, from a more specialized doctor during surgery, the assistance can be automatically performed on the surgeon by the assistance system 100.

In the database 110 of metadata, metadata of situations obtained on the basis of surgery results and the like in the past, which are generated in accordance with the above-mentioned database generation method, is stored in advance. In the database 120 of parameters, parameters of assistance performed with respect to situations, which are made to correspond to the metadata (situations), are stored in advance. The metadata and the parameters respectively stored in the database 110 of metadata and the database 120 of parameters have been described above, and thus the descriptions will be omitted here.

The control unit 5063 refers to the image recognition result and the metadata subjected to the image recognition by the object recognition image processing unit 130 on the basis of the first image obtained by picking up the image of the surgical part including the surgery target site, calculates the metadata of the situation which is close to the image recognition result, and extracts this parameter made to correspond to the calculated metadata. Then, assistance, for example, image quality adjustment of the image, switching of irradiation light of the camera, and camera control such as adjustment of the scale and the focal point, display of the second image after the image quality adjustment and after the camera control, display of an image or video in a past dangerous event which is generated in a similar situation, display of past surgery video in the similar situation, reporting advice, fluorescence, and the like, and the like is performed in accordance with that parameter.

Next, the specific assistance performed by the above-mentioned assistance system 100 will be described in first to eighth embodiments, hereinafter.

In the following embodiment, in the endoscopic surgery (or the examination) using the above-mentioned assistance system, the insertion portion of the camera head 5005 is inserted into the body of the patient, and an image of the surgical part is picked up by the image pickup unit 5009 in a state in which the surgical part of the patient is irradiated with light radiated from a distal end of the insertion portion of the camera head 5005. The insertion of the camera head 5005 into the body and the image pickup of the surgical part are similar in all of the embodiments below. Therefore, the descriptions will be omitted.

A live image (first image) picked up by the image pickup unit 5009 under normal light (white light), an image (second image) to be assistance for the surgeon 5067 which is suitable for the situation shown in this first image, and the like are basically displayed on the display apparatus 5041. The surgeon 5067 performs surgery, examination, or diagnosis while viewing the image displayed on the display apparatus 5041.

First Embodiment

The description will be made by exemplifying endoscopic examination of a stomach. In this embodiment, a description will be made by taking an example in which assistance to display an inflammation state of gastritis in an emphasis state is performed.

Figure 6:
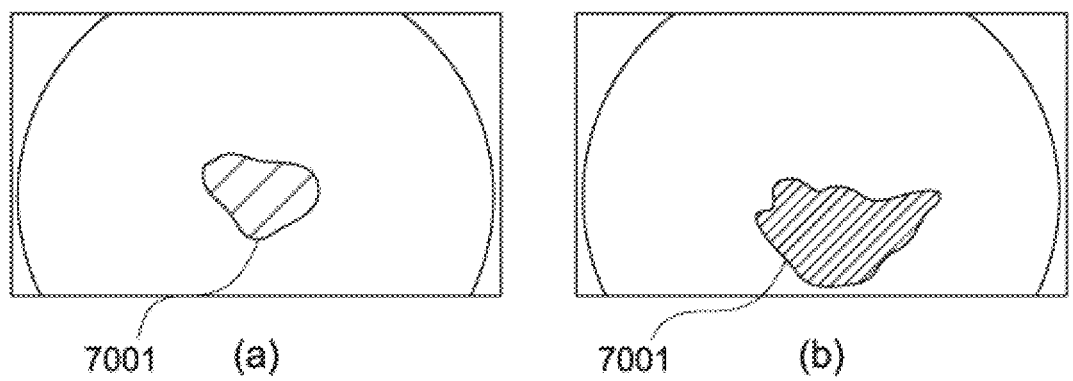
FIG. 6 A view depicting images of an inner wall of a stomach before and after image quality adjustment in an assistance system according to a first embodiment.

FIG. 6 shows an image of the inside of the stomach. FIG. 6(a) is an image (first image) of a surgical part including a site (affected part) which is a surgical target, which is picked up by the image pickup unit 5009. FIG. 6(b) is a second image obtained in such a manner that the image quality of the first image is adjusted in accordance with the parameter extracted by the control unit 5063. The second image is an image to be assistance for the surgeon 5067. Here, the first image shows the image acquired by irradiating the surgical part with normal light (white light) and picking up an image and the surgical part in a natural tone can be observed in observation with the normal light. The second image is the image in which the assistance suitable for the situation has been performed on the basis of the first image and the same applies to the following descriptions.

The first image and the second image are displayed on the display apparatus 5041. The first image is displayed after the outline of the image, the brightness of the screen, the contrast, and the like are adjusted by the image processing unit 5061 of the CCU 5039.

In a case where the purpose, the target organ, and the like are clear, for example, in a case of endoscopic examination of the stomach, those pieces of information are input in the endoscopic surgery system 5000 in advance before examination.

The control unit 5063 causes the object recognition image processing unit 130 to extract characteristics from the first image picked up by the image pickup unit 5009 and to perform image recognition. The control unit 5063 calculates the metadata of the situation similar to the image recognition result from the database 110 of metadata.

Next, the control unit 5063 extracts the parameter of the image quality adjustment made to correspond to the calculated metadata from the database 120 of parameters. The control unit 5063 causes the image processing unit 5061 to perform image processing on the first image in accordance with this extracted parameter of the image quality adjustment and to generate the second image. The generated second image is displayed on the display apparatus 5041.

In this embodiment, the detection result of the surgical part including the affected part, for example, the kind of surgical procedure (in this embodiment, the gastritis), the purpose (in this embodiment, the examination), the color components (R, G, B) of the surgical part, the image gradient information, the texture pattern, and the like is used as the metadata. Then, the parameter of the image quality adjustment of linked color imaging (LCI (registered trademark)) is made to correspond to this metadata. The LCI can perform image processing to increase a chroma difference, a hue difference of the color close to the color of the mucous membrane and perform image processing to emphasize a slight color difference.

In FIG. 6, a region in which there is a color difference from the normal mucous membrane is drawn with diagonal lines and displayed and a state having a smaller color difference from the normal mucous membrane is shown as the line distance between the oblique lines becomes wider. As depicted in FIG. 6(a), in the first image before image quality adjustment, it is difficult to recognize a light color difference between the normal mucous membrane and a mucous membrane (affected part) 7001 with inflammation, and it is difficult to judge whether or not it is the affected part. In contrast, as depicted in FIG. 6(b), the second image whose image quality is adjusted is subjected to image processing such that a slight color difference of the mucous membrane is emphasized. With this configuration, the surgeon 5067 views the second image displayed such that the affected part 7001 is emphasized, which is shown in FIG. 6(b), and the state of the inflammation and the range of the inflammation can be more correctly understood. A more suitable diagnosis can be performed.

In general, switching of the image quality adjustment is manually performed by the user and, for example, it is not practical to frequently perform image quality adjustment during the surgery.

In contrast, in the assistance system in this embodiment, the parameter corresponding to the situation of the surgical part is extracted on the basis of the first image picked up by the image pickup unit 5009 and the metadata, the image quality adjustment of the first image is performed in accordance with this parameter, and the second image is automatically generated and displayed. Thus, the surgeon 5067 can view the automatically displayed second image and perform surgery, examination, or diagnosis without taking the trouble to perform an image quality adjustment operation.

Second Embodiment

The description will be made with reference to FIGS. 7 to 9 by exemplifying endoscopic rectal polyp mucosal resection. In this embodiment, in a case of a situation where a polyp is present, assistance to switch the irradiation light and display the polyp in an enlarged state by adjusting the scale and the focal point is performed.

Figure 7:
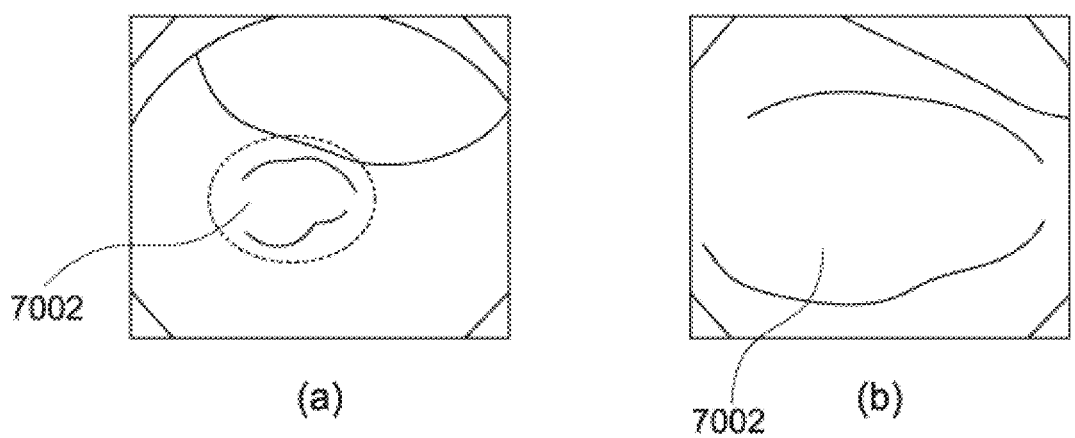
FIG. 7 A view depicting an example of a colon polyp image and an enlarged display image thereof displayed on a display apparatus in an assistance system according to a second embodiment.
Figure 8:
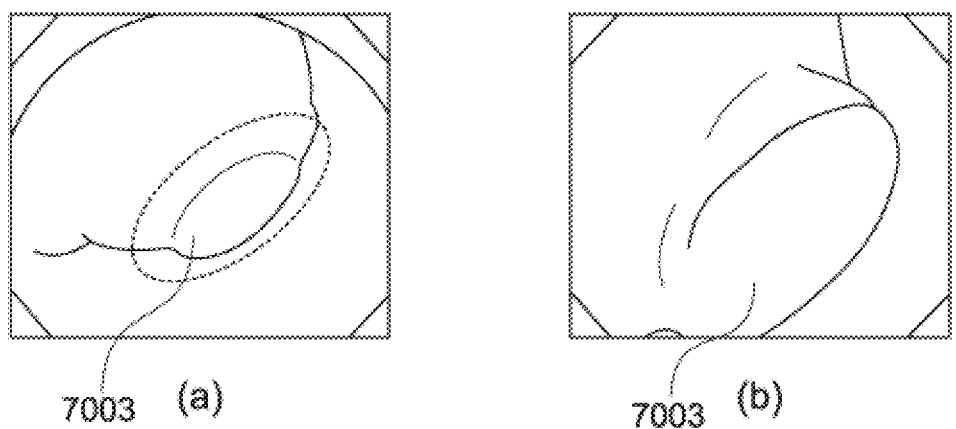
FIG. 8 A view depicting another example of the colon polyp image and an enlarged display image thereof displayed on the display apparatus in the assistance system according to the second embodiment.
Figure 9:
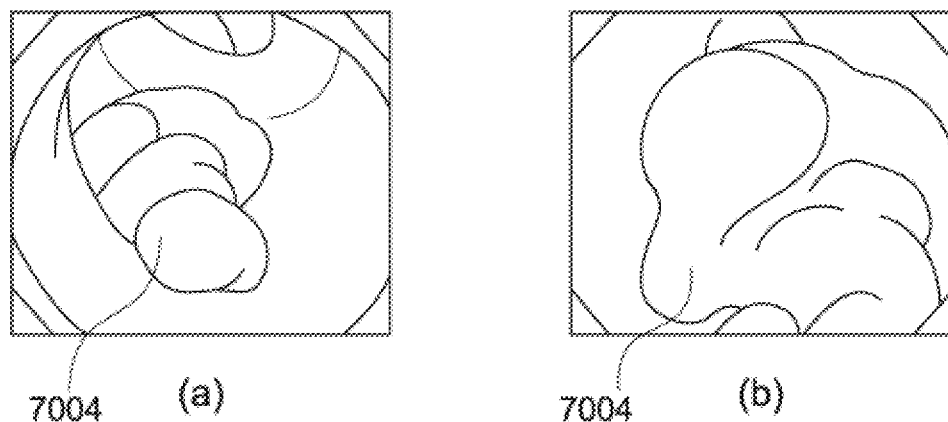
FIG. 9 A view depicting still another example of the colon polyp image and an enlarged display image thereof displayed on the display apparatus in the assistance system according to the second embodiment.

FIGS. 7 to 9 show an image of the inside of a colon with a colon polyp.

FIG. 7(a) shows an image (first image) of a site (affected part) 7002 of a surgical target, which is picked up by the image pickup unit 5009. FIG. 7(b) shows a second image acquired in accordance with the parameter extracted by the control unit 5063 and is an enlarged display image of the affected part 7002.

FIG. 8(a) shows an image (first image) of a site (affected part) 7003 of a surgical target as another case, which is picked up by the image pickup unit 5009. FIG. 8(b) shows a second image acquired in accordance with the parameter extracted by the control unit 5063 and is an enlarged display image of the affected part 7003.

FIG. 9(a) shows an image (first image) of a surgical part including a site (affected part) 7004 of a surgical target as still another case, which is picked up by the image pickup unit 5009. FIG. 9(b) shows a second image acquired in accordance with the parameter extracted by the control unit 5063 and is an enlarged display image of the affected part 7004.

In FIG. 7(a) and FIG. 8(a), the region surrounded by the dotted line is a polyp (affected part) and FIG. 7(b) and FIG. 8(b) correspond to the enlarged display image of this polyp.

First of all, those pieces of information are input in the endoscopic surgery system 5000 before the surgery in advance in a case where the kind of surgical procedure, the purpose, and the target affected part are clear, for example, in a case of rectal polyp mucosal resection.

The control unit 5063 causes the object recognition image processing unit 130 to extract characteristics from the first image picked up by the image pickup unit 5009 and to perform image recognition. The control unit 5063 calculates metadata of the situation similar to the image recognition result on the basis of the database 110 of metadata.

Next, the control unit 5063 extracts the parameter of the camera control made to correspond to the calculated metadata from the database 120 of parameters. The control unit 5063 adjusts the scale and the focal point of the picked up image in accordance with this extracted parameter of the camera control and changes the image pickup condition to switch the irradiation light to narrow band imaging (NBI). Then, the control unit 5063 causes the image pickup unit 5009 to pick up an image of the surgical part under an image pickup condition after the change, acquires the second image, and causes the display apparatus 5041 to display it. The second image is controlled so as to be displayed in an enlarged state using the center position of the polyp as a center on the basis of the image recognition result of the first image.

In this embodiment, the kind of surgical procedure (in this embodiment, the colon polyp), the purpose (in this embodiment, resection), the target affected part (in this embodiment, the rectum), the color components (R, G, B) of the surgical part, the detection result of the surgical part including the affected part such as the image gradient information, the texture pattern, and the like, and the like are used as the metadata. Then, a camera control parameter, for example, adjustment of the scale and the focal point for displaying the polyp in an enlarged state and switching to narrow band light of irradiation light for narrow band imaging (NBI) is made to correspond to this metadata.

The second image is an image in which the polyp is displayed in an enlarged state and an image in which superficial blood vessels are emphasized is provided by using the NBI for the irradiation light. The surgeon 5067 can more correctly check the state of the polyp and the range of the polyp with this second image. Thus, it is possible to prevent an unnecessarily large part including the polyp from being resected or prevent the polyp from being left by resecting a small part of the polyp on the contrary. More suitable surgery can be performed.

In general, the surgeon 5067 needs to perform operations of a procedure of moving the camera head inside the colon, finding the polyp, displaying it in an enlarged state, and changing the image pickup method (changing the irradiation light). However, such an operation is complicated and it is difficult to perform this operation on the entire inner wall of the colon during the surgery.

In contrast, in the assistance system in this embodiment, a parameter suitable for the surgery situation is extracted on the basis of the first image picked up by the image pickup unit 5009 and the metadata, the scale and focal point control of the camera and the irradiation light switching operation are automatically performed in accordance with this parameter, and the second image is generated and displayed.

Therefore, only by the surgeon 5067 moving the camera head 5005 inside the colon, the polyp can be found by the assistance system 100 and in addition, the image pickup condition is automatically changed, and the enlarged display image of the polyp in the state suitable for observation can be obtained. With this configuration, suitable surgery can be performed without need for performing a complicated process during the surgery.

Third Embodiment

The description will be made with reference to FIGS. 10 to 12 by exemplifying endoscopic rectal polyp mucosal resection as in the second embodiment. In this embodiment, an example of determination of similarity between an image recognition result of a first image and metadata for calculating the metadata will be described.

Further, in the third embodiment, a first image is displayed as a main screen and a second image whose image quality is adjusted in accordance with an extracted parameter is displayed as a sub-screen in a single display apparatus 5041.

Figure 10:
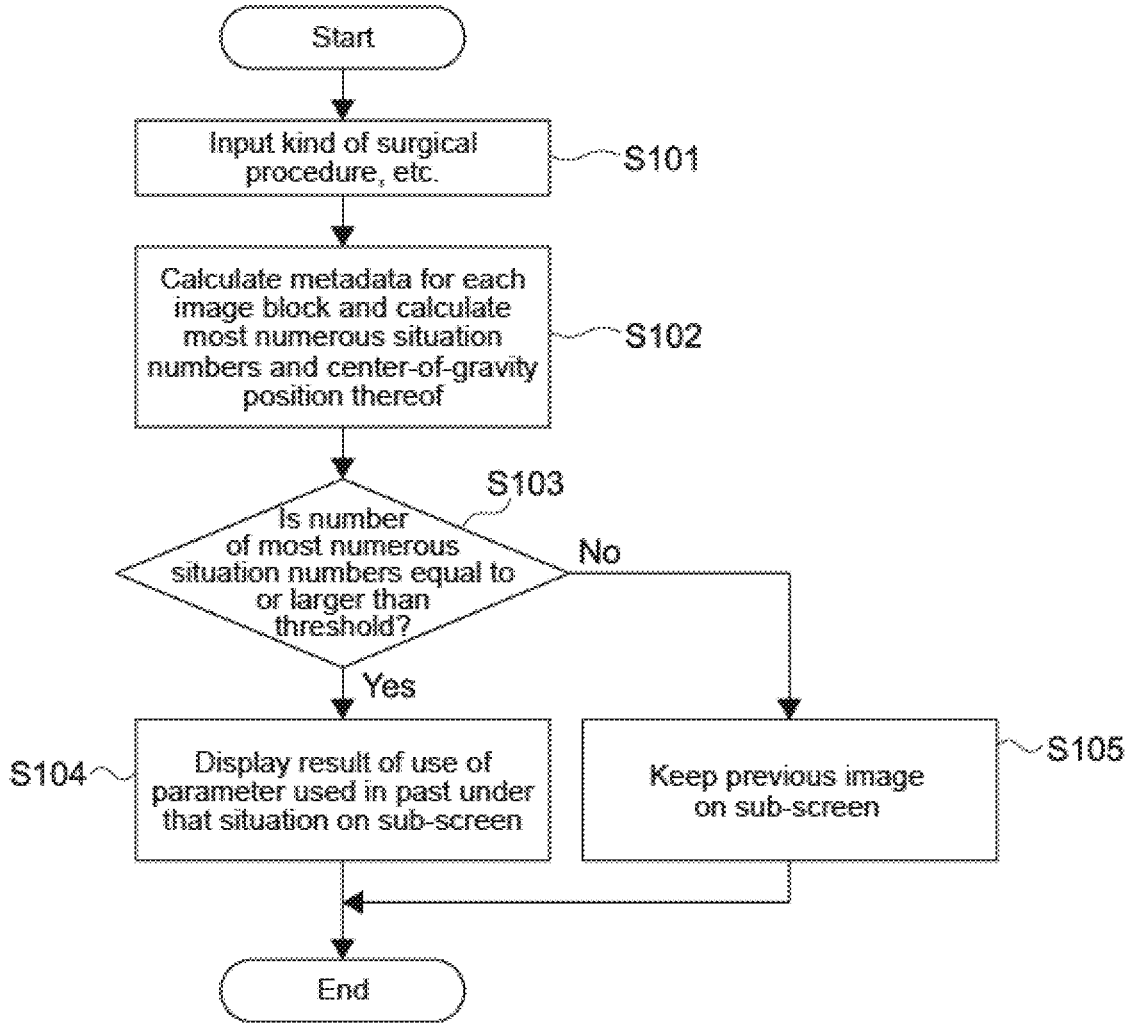
FIG. 10 A view depicting an information processing method in an assistance system according to a third embodiment.
Figure 11:
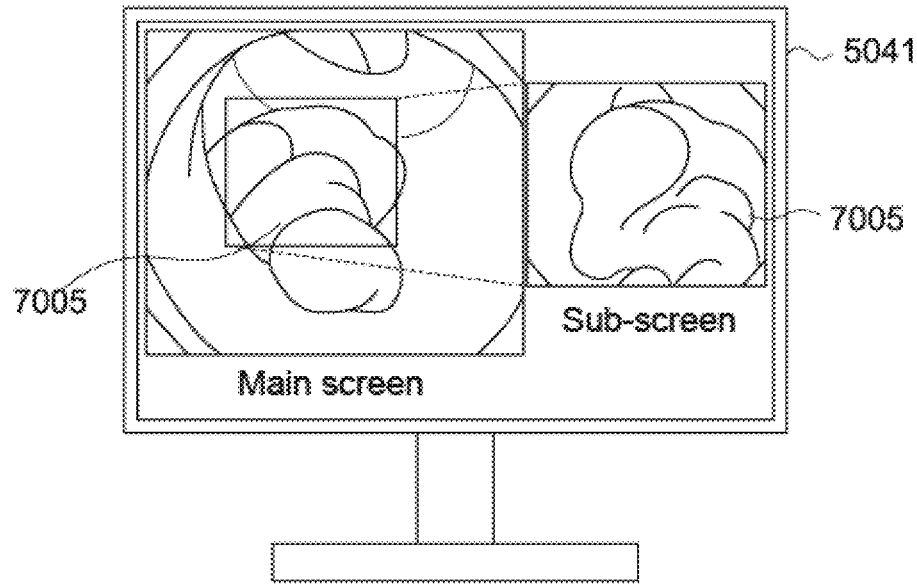
FIG. 11 A view depicting an example of a screen displayed on a display apparatus of the assistance system according to the third embodiment.

FIG. 10 is a diagram depicting an information processing method according to determination of similarity between the image recognition result of the first image and the metadata for calculating the metadata. FIG. 11 is a diagram depicting a screen displayed on the display apparatus 5041. FIG. 12 is a diagram for describing determination of similarity between an image recognition result of an image (first image) of a surgical part including a site (affected part) of a surgical target, which is picked up by the image pickup unit 5009, and metadata.

Hereinafter, the description will be made in accordance with the flow of FIG. 10.

In a case where the kind of surgical procedure, the purpose, and the target affected part are clear, for example, in a case of the endoscopic rectal polyp mucosal resection, those pieces of information are input in the endoscopic surgery system 5000 by the surgeon 5067 before the surgery in advance (S101).

In the display apparatus 5041, the image (first image) of the surgical part including the affected part (in this embodiment, the polyp) 7005 is displayed on the main screen and the enlarged display image (second image) of the polyp 7005 is displayed on the sub-screen.

The control unit 5063 causes the object recognition image processing unit 130 to extract characteristics from the first image picked up by the image pickup unit 5009 and causes image recognition to be performed. The control unit 5063 performs determination of similarity between this image recognition result and the metadata.

Here, the determination method for similarity between the image recognition result and the metadata will be described with reference to FIG. 12.

Figure 12:
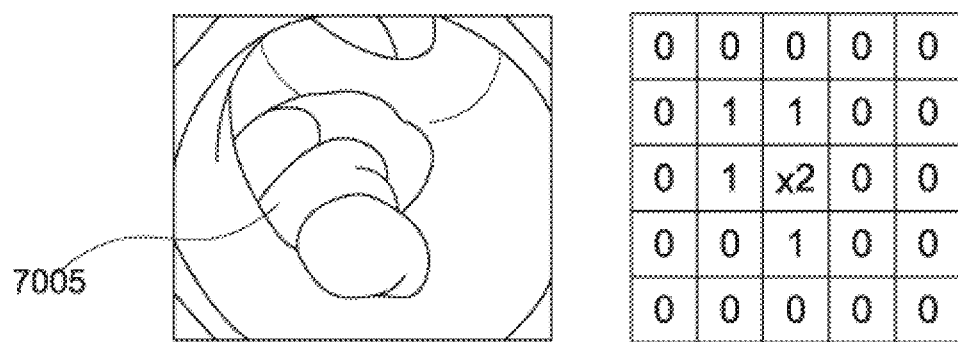
FIG. 12 A view depicting an example of determination of similarity between an image recognition result and metadata in the assistance system according to the third embodiment.

As depicted in FIG. 12, the control unit 5063 divides the first image into multiple image blocks and causes the object recognition image processing unit 130 to perform image recognition for each image block.

In this embodiment, the kind of surgical procedure (in this embodiment, the colon polyp), the purpose (in this embodiment, the mucosal resection), the target affected part (in this embodiment, the rectum), the kind of affected part (in this embodiment, the adenomatous polyp), the color components (R, G, B) of the surgical part, the detection result of the surgical part including the affected part such as the image gradient information, the texture pattern, and the like, and the like are used as the metadata.

The control unit 5063 calculates metadata similar to the image recognition result for each image block and gives a situation number of the metadata similar to the image recognition result.

The control unit 5063 calculates a situation number largest in number of image blocks among the given situation numbers and a center-of-gravity position of the image blocks to which such situation numbers are given (S102).

Here, the situation number is a number given for distinguishing multiple situations, in which metadata such as the kind of surgical procedure, the purpose, and the target affected part are common and the metadata of the detection result of the surgical part is different. For example, exemplifying colon polyps, colon polyps also have various shapes, sizes, and states and multiple situations are present. The situation number is given for distinguishing such multiple situations.

In FIG. 12, an image block in which 0 is displayed indicates that the similar metadata is absent. An image block in which 1 is displayed indicates that the metadata according to the situation 1 is similar to the image recognition result. An image block in which 2 is displayed indicates that the metadata according to the situation 2 is similar to the image recognition result. An image block in which "x" is displayed indicates the center of gravity of the image blocks of the situation larger in number between the situation 1 and the situation 2.

As depicted in FIG. 12, in S102, the first image is divided into multiple image blocks, an image recognition result is calculated for each image block, the image recognition result and the metadata are referred to for each image block, and the situation number of the similar metadata is given. As depicted in FIG. 12, the most given situation numbers are 1 and the center-of-gravity position (in the figure, the position shown as "x") of the image blocks to which those most numerous situation numbers 1 are given is calculated.

Next, the control unit 5063 determines whether or not the number of most numerous situation numbers, the number of situation numbers 1 in this embodiment, is equal to and larger than a threshold (S103).

If determining Yes in S103, the control unit 5063 changes the image pickup condition in accordance with the parameter made to correspond to the metadata of the situation number 1, picks up an image of the surgical part such that the calculated center-of-gravity position becomes the center, acquires the second image, and causes the display apparatus 5041 to display the image (S104). As depicted in FIG. 12, the first image is displayed as a main screen and the second image is displayed as a sub-screen in the display apparatus 5041.

If determining No in S103, the control unit 5063 causes the image which has already been displayed on the sub-screen to be kept (S105). With this configuration, for example, the surgeon 5067 can perform surgery by viewing the second image in which the affected part is displayed in an emphasized state and is displayed in an enlarged state and can perform more suitable surgery.

Fourth Embodiment

The description will be made with reference to FIGS. 13 and 14 by exemplifying the endoscopic rectal polyp mucosal resection. In this embodiment, in a case where the situation shown in the first image is similar to the past dangerous event, assistance to display and reproduce the video in the past dangerous event is performed. Here, the metadata according to the situation when the past dangerous event occurs is made to correspond to the parameter of display of the video in the past dangerous event. It should be noted that although displaying the video in the past dangerous event generated under the similar situation as reference video is shown here as an example, it is not limited to the video or image in the dangerous event and the video or image of the surgery performed in the past under the similar situation to be a reference may be displayed as the reference video or image.

Figure 13:
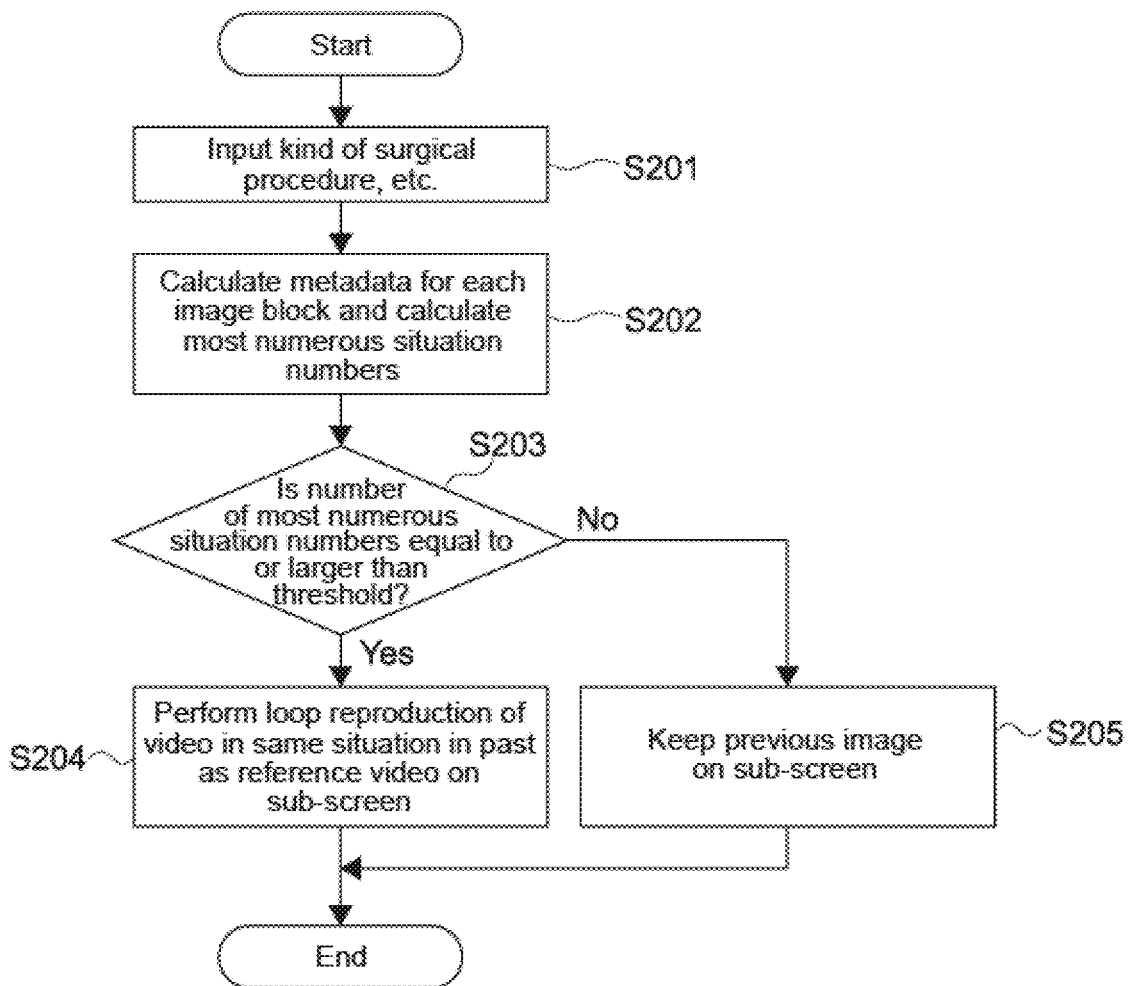
FIG. 13 A view depicting an information processing method in an assistance system according to a fourth embodiment.

FIG. 13 is a diagram depicting an information processing method according to this embodiment. FIG. 14 is a diagram depicting a screen displayed on the display apparatus 5041.

Hereinafter, the description will be made in accordance with the flow of FIG. 13.

First of all, in a case where the kind of surgical procedure, the purpose, and the target affected part are clear, for example, in a case of the endoscopic surgery of the rectal polyp, those pieces of information are input into the endoscopic surgery system 5000 by the surgeon 5067 before the surgery in advance (S201).

As in third embodiment, the control unit 5063 causes the object recognition image processing unit 130 to extract characteristics from the first image picked up by the image pickup unit 5009 and to perform image recognition for each image block. The control unit 5063 calculates metadata similar to the image recognition result for each image block and gives the situation number of the similar metadata.

The control unit 5063 calculates a situation number largest in number of image blocks given among the given situation numbers (S202). Next, the control unit 5063 determines whether or not the number of most numerous situation numbers is equal to and larger than a threshold (S203).

If determining Yes in S203, the control unit 5063 considers that the situation (image recognition result) shown in the first image is similar to the past dangerous event situation (metadata) of the most given situation numbers and causes the display apparatus 5041 to display reference video in the past dangerous event, for example, bleeding or the like, which is the parameter made to correspond to this metadata (S204).

Figure 14:
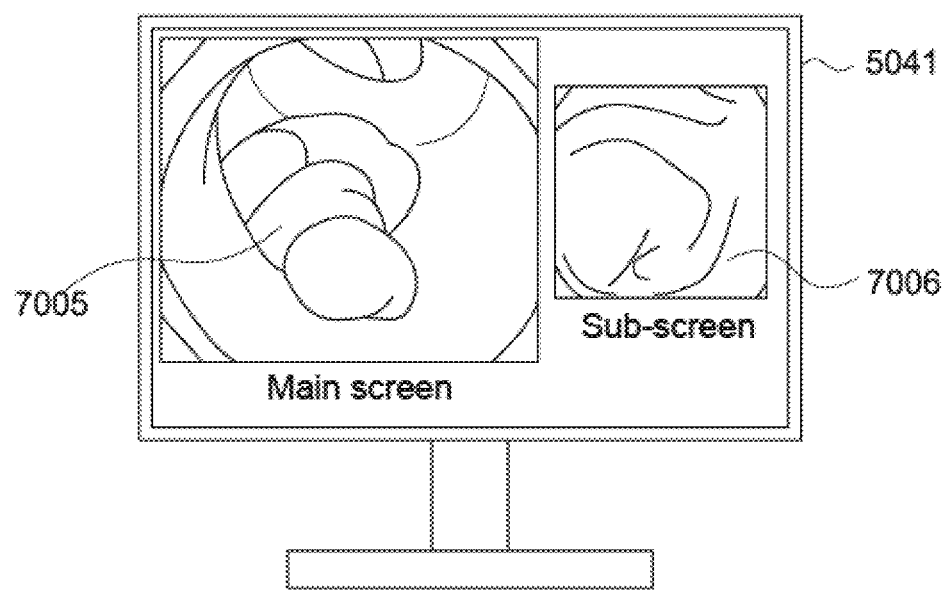
FIG. 14 A view depicting an example of a screen displayed on a display apparatus of the assistance system according to the fourth embodiment.

As depicted in FIG. 14, the first image which is the live image picked up by the image pickup unit 5009 is displayed on the main screen and reference video 7006 in the past dangerous event is displayed on the sub-screen in the display apparatus 5041. The reference video in this past dangerous event is subjected to loop reproduction. In FIG. 14, the reference sign 7005 indicates a polyp.

If determining No in S203, the control unit 5063 causes the image which has already been displayed on the sub-screen to be kept (S204).

With this configuration, the surgeon 5067 refers to the reference video in the past dangerous event, for example, bleeding or the like to thereby predict danger and perform more suitable surgery so as to avoid it.

Fifth Embodiment

The description will be made with reference to FIGS. 15 and 16 by exemplifying the endoscopic colon polyp mucosal resection. During the surgery, there is a case where low visibility is caused by smoke and the like generated when cutting an affected part with a radio knife. In this embodiment, in a case of a situation where the first image which is the live image is in a low-visibility state, assistance to cause the first image before the low visibility is caused to be displayed on the sub-screen. Here, a parameter of causing the first image before the low visibility is caused to be displayed on the sub-screen is made to correspond to the metadata according to the situation where the low visibility was provided in the past.

Figure 15:
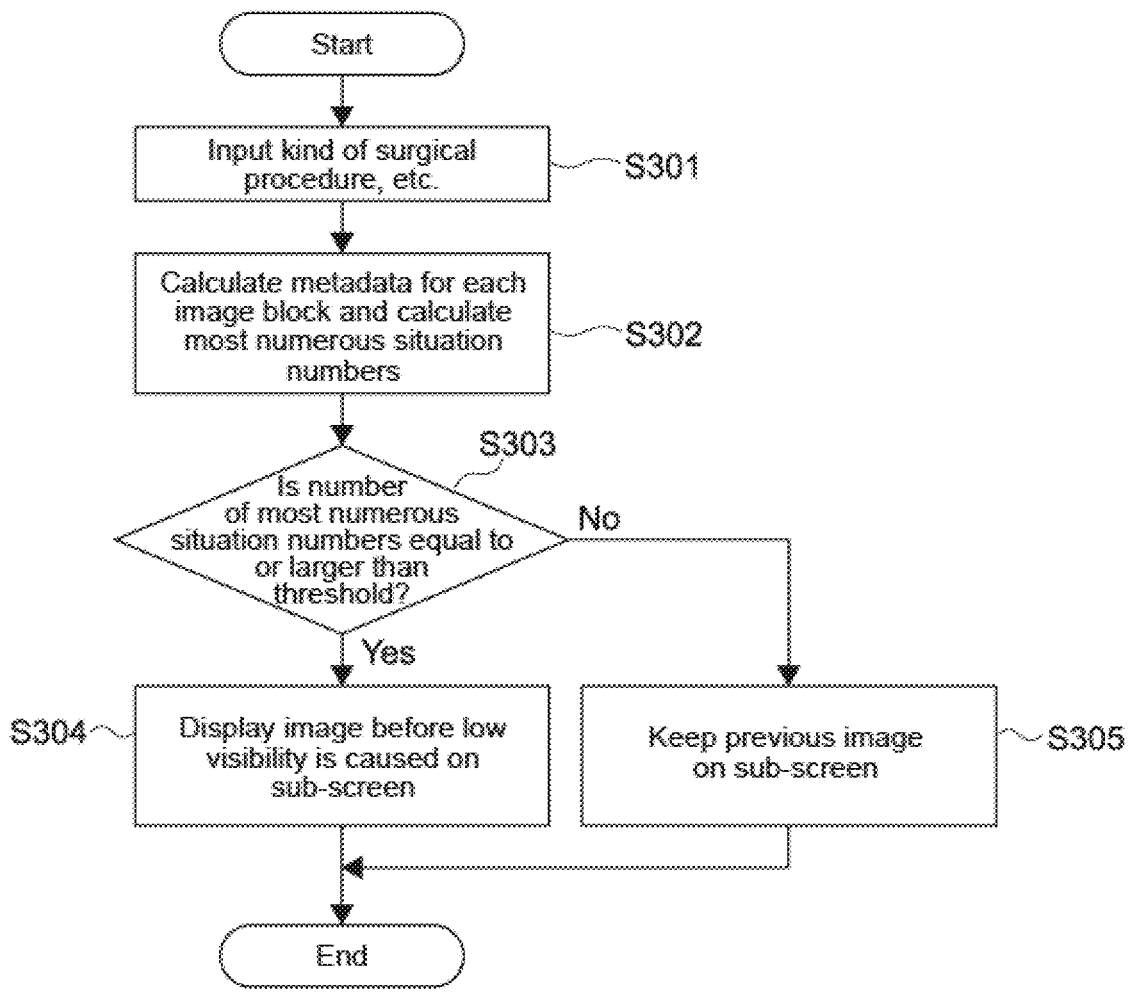
FIG. 15 A view depicting an information processing method in an assistance system according to a fifth embodiment.
Figure 16:
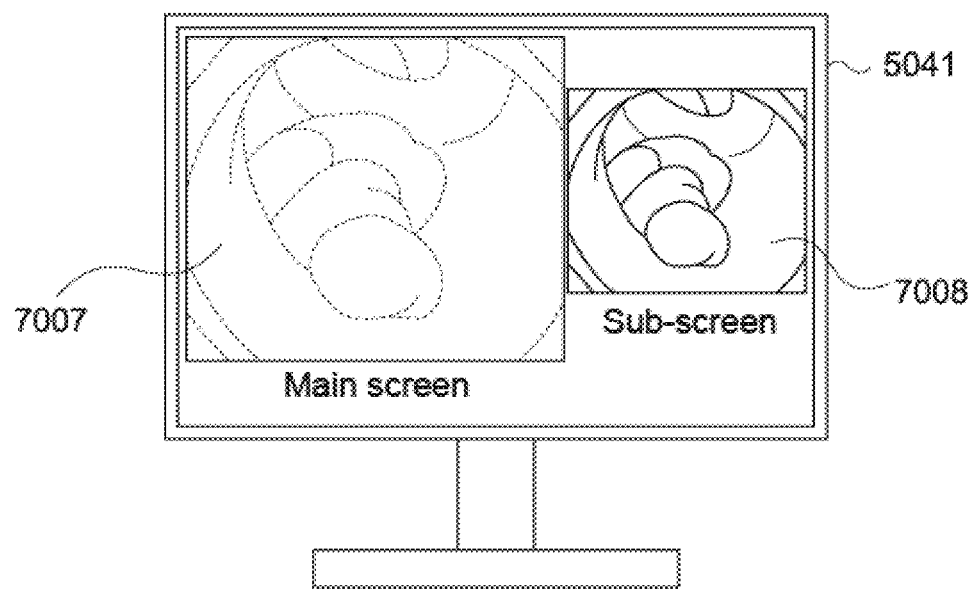
FIG. 16 A view depicting an example of a screen displayed on a display apparatus of the assistance system according to the fifth embodiment.

FIG. 15 is a diagram depicting an information processing method according to this embodiment. FIG. 16 is a diagram depicting a screen displayed on the display apparatus 5041.

Hereinafter, the description will be made in accordance with the flow of FIG. 15.

First of all, in a case where the purpose of the surgery, the kind of operative surgical procedure, the target organ, and a target surgical part are clear, for example, in a case of the endoscopic surgery of the colon polyp, those pieces of information are input into the endoscopic surgery system 5000 by the surgeon 5067 before the surgery in advance (S301).

In the display apparatus 5041, an image (first image) 7007 of the surgical part including the affected part (in this embodiment, the polyp) is displayed on the main screen and the second image (enlarged display image of the polyp) acquired in accordance with the acquisition method for the second image of the second embodiment is displayed on the sub-screen, for example. Here, the low visibility is caused by smoke and the like generated by cutting with the radio knife during the surgery.

As in the third embodiment, the control unit 5063 causes the object recognition image processing unit 130 to extract characteristics from the first image picked up by the image pickup unit 5009 to perform image recognition for each image block. The control unit 5063 calculates the metadata similar to the image recognition result for each image block and gives the situation number of the similar metadata. The control unit 5063 calculates a situation number largest in number of image blocks among the given situation numbers (S302). Next, the control unit 5063 determines whether or not the number of most numerous situation numbers is equal to and larger than a threshold (S303).

If determining Yes in S303, the control unit 5063 considers that the situation (image recognition result) shown in the first image is similar to the situation of low visibility (metadata) and causes the first image before the low visibility is caused to be displayed on the sub-screen in accordance with the parameter made to correspond to this metadata (S304). As depicted in FIG. 16, the first image 7007 which is a live image having low visibility, which is picked up by the image pickup unit 5009, is displayed on the main screen and the first image before the low visibility is caused is displayed as a second image 7008 on the sub-screen in the display apparatus 5041.

If determining No in S303, the control unit 5063 causes the image which has already been displayed on the sub-screen to be kept (S304).

With this configuration, even when the low visibility occurs, the surgeon 5067 can ensure the field of view by viewing the image before the low visibility is caused.

Sixth Embodiment

The description will be made with reference to FIGS. 17 and 18 by exemplifying intracavitary anastomosis using a stapler in endoscopic surgery. When performing anastomosis on a tissue with the stapler during the surgery, there is a case where the ends of the stapler do not correctly hold the tissue and fails to perform anastomosis. In this embodiment, in a case of a situation where the ends of the stapler are not shown in the first image or a case of a situation where there is a possibility that the ends of the stapler do not correctly hold the tissue, assistance to report displaying warning on the screen is performed considering that there is a possibility that the anastomosis fails.

Figure 17:
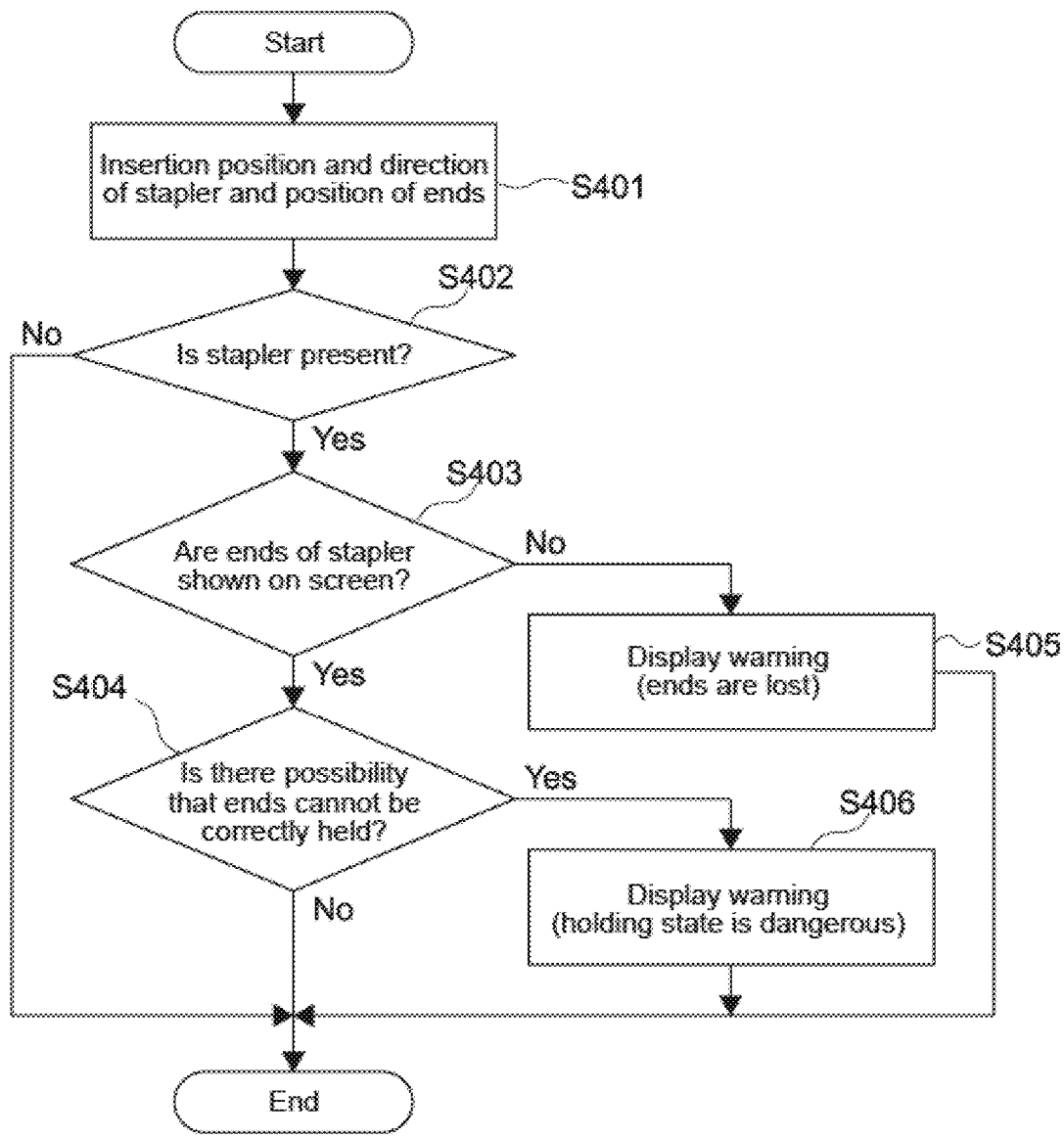
FIG. 17 A view depicting an information processing method in an assistance system according to a sixth embodiment.

FIG. 17 is a diagram depicting an information processing method according to this embodiment. FIG. 18 is a diagram depicting a screen displayed on the display apparatus 5041.

Hereinafter, the description will be made by exemplifying a case of performing anastomosis using a stapler 7009 in reconstructive surgery in accordance with the flow of FIG. 17.

The control unit 5063 causes the object recognition image processing unit 130 to extract characteristics from the first image picked up by the image pickup unit 5009 and to perform image recognition. The control unit 5063 calculates similar metadata on the basis of the image recognition result. Here, the presence and absence of the surgical tool (in this embodiment, the stapler), the position of the surgical tool in the image, the situation of the surroundings, and the like are used as the metadata.

The calculation of the similar metadata is performed in accordance with S402 to S404 shown below.

The control unit 5063 calculates an insertion position and a direction of the stapler 7009 and positions of the ends on the basis of the image recognition result of the first image by the object recognition image processing unit 130 (S401). Next, the control unit 5063 determines whether or not the stapler 7009 is present in the first image on the basis of the calculation result (S402). The first image is displayed on the display apparatus 5041.

If determining No in S402, the processing is terminated and warning is not displayed.

If determining Yes in S402, the control unit 5063 determines whether or not the ends of the stapler 7009 are shown within the screen (S403).

Figure 18:
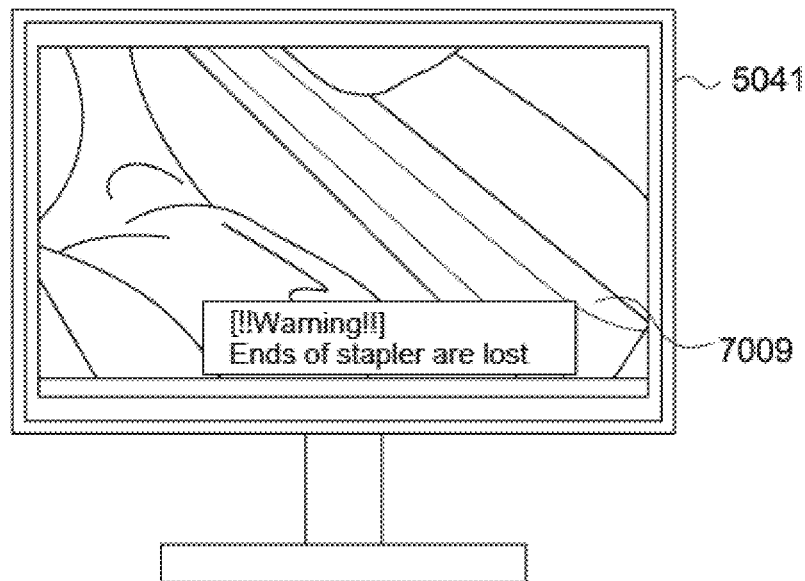
FIG. 18 A view depicting an example of a screen displayed on a display apparatus of the assistance system according to the sixth embodiment.

If determining No in S403, the control unit 5063 performs reporting by causing the display apparatus 5041 to display warning saying "Ends of the stapler are lost" as depicted in FIG. 18 (S405).

If determining Yes in S403, the processing proceeds to S404. In S404, the control unit 5063 determines whether or not there is a possibility that the ends of the stapler 7009 fail to correctly perform holding.

If determining No in S404, the processing is terminated and warning is not displayed. If determining Yes in S404, reporting is performed by causing the display apparatus 5041 to display warning saying "Holding state is dangerous" (S406).

In this embodiment, the parameter of reporting of displaying warning saying "Ends are lost" is made to correspond to the metadata of the situation where the stapler is present within the screen (presence and absence of the surgical tool) and the ends of the stapler are not shown within the screen (position of the surgical tool in the image).

Further, the parameter of reporting of displaying warning saying "Holding state is dangerous" is made to correspond to the metadata of the situation where the stapler is present within the screen (presence and absence of the surgical tool), the ends of the stapler are shown within the screen (position of the surgical tool in the image), and the ends of the stapler fail to correctly perform holding (situation of the surroundings).

With this configuration, the surgeon 5067 can predict occurrence of a failure of anastomosis by the stapler 7009 and suitably cope with it. It should be noted that here, the stapler has been exemplified as the surgical tool, though not limited thereto. For example, it is also applicable to an energy device. Further, here, reporting is performed to the surgeon 5067 by displaying the warning on the display apparatus 5041, though not limited thereto. For example, reporting may be performed as sound.

As described above, more suitable surgery can be performed in such a manner that assistance in which reporting advice or warning suitable for the situation is performed is performed.

Seventh Embodiment

The description will be made with reference to FIGS. 19 and 20 by exemplifying endoscopic examination of a stomach. In this embodiment, in a case of a situation where it is highly likely that a part of interest is an affected part (lesion site), assistance in which a second image emphasized by changing the irradiation light into the special light and picking up an image is displayed is performed.

Figure 19:
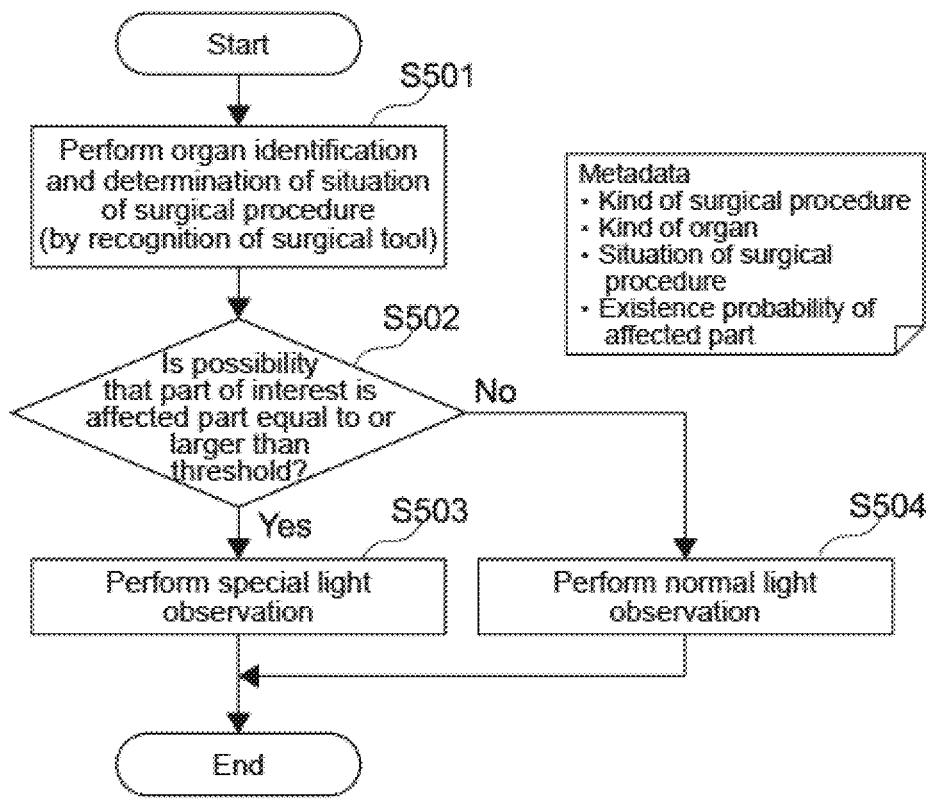
FIG. 19 A view depicting an information processing method in an assistance system according to a seventh embodiment.

FIG. 19 is a flowchart depicting an information processing method in this embodiment. FIG. 20 is a diagram depicting images of a surgical part before and after image processing in this embodiment.

The description will be made in accordance with the flow of FIG. 19.

The control unit 5063 causes the object recognition image processing unit 130 to extract characteristics from the first image picked up by the image pickup unit 5009 and to perform image recognition. With this configuration, an organ is determined by surgical tool recognition and the situation of the surgical procedure and the like are determined (S501).

Next, the control unit 5063 calculates the metadata similar to the image recognition result on the basis of the database 110 of metadata. The kind of surgical procedure, the kind of organ, the situation of the surgical procedure, the existence probability of the affected part (lesion part), and the like are used as the metadata.

In the control unit 5063, the irradiation light at the time of observation is controlled in accordance with the parameter made to correspond to the calculated metadata. If regarding the calculated metadata, the existence probability of the affected part, i.e., the possibility that the part of interest is the affected part is equal to or larger than the threshold, the parameter of the special light observation is made to correspond to this metadata and control is performed such that the irradiation light at the time of observation becomes the special light. On the other hand, if the calculated metadata is the metadata in which the existence probability of the affected part, i.e., the possibility that the part of interests is the affected part is lower than the threshold, the parameter of the normal light (white light) observation is made to correspond to this metadata and control is performed such that the irradiation light at the time of observation becomes the normal light.

The calculation of the metadata similar to the image recognition result is performed as follows. The control unit 5063 determines whether or not the possibility that the part of interest is the affected part is equal to or higher than the threshold (S502). If determining Yes in S502, the control unit 5063 performs control such that the irradiation light becomes the special light (S503). On the other hand, if determining No in S502, the control unit 5063 performs control such that the irradiation light becomes the normal light (S504).

FIG. 20(*a*) is an image picked up under irradiation with the normal light by the image pickup unit 5009 and FIG. 20(*b*) shows an image picked up under irradiation with the special light. In FIG. 20, the reference sign 7010 indicates a blood vessel and the reference signs 7012 indicates an affected part (lesion site). In FIG. 20(*a*), the blood vessel 7010 not easy to be identified in the image is depicted as the dotted line. Although the affected part 7012 and the blood vessel 7010 have not been clear in the normal light observation as depicted in FIG. 20, the blood vessel 7010 can be identified in the special light observation and image display by which the position of the affected part 7012 is easily determined is provided. The image obtained by the image pickup with special light is displayed on the display apparatus 5041. In this manner, the image emphasized by switching to the image pickup with special light can be obtained and a more accurate diagnosis can be performed.

Eighth Embodiment

The description will be made with reference to FIGS. 21 and 22 by exemplifying a case where the amount of bleeding is large and it becomes difficult to identify the tissue during the surgery. In this embodiment, in a case of a situation where it is difficult to identify the tissue due to bleeding, assistance in which the second image in which identification of the tissue is clear, which is obtained in such a manner that image pickup is performed using the irradiation light as special light for transmission through blood and the bleeding part is removed, is displayed is performed.

Figure 21:
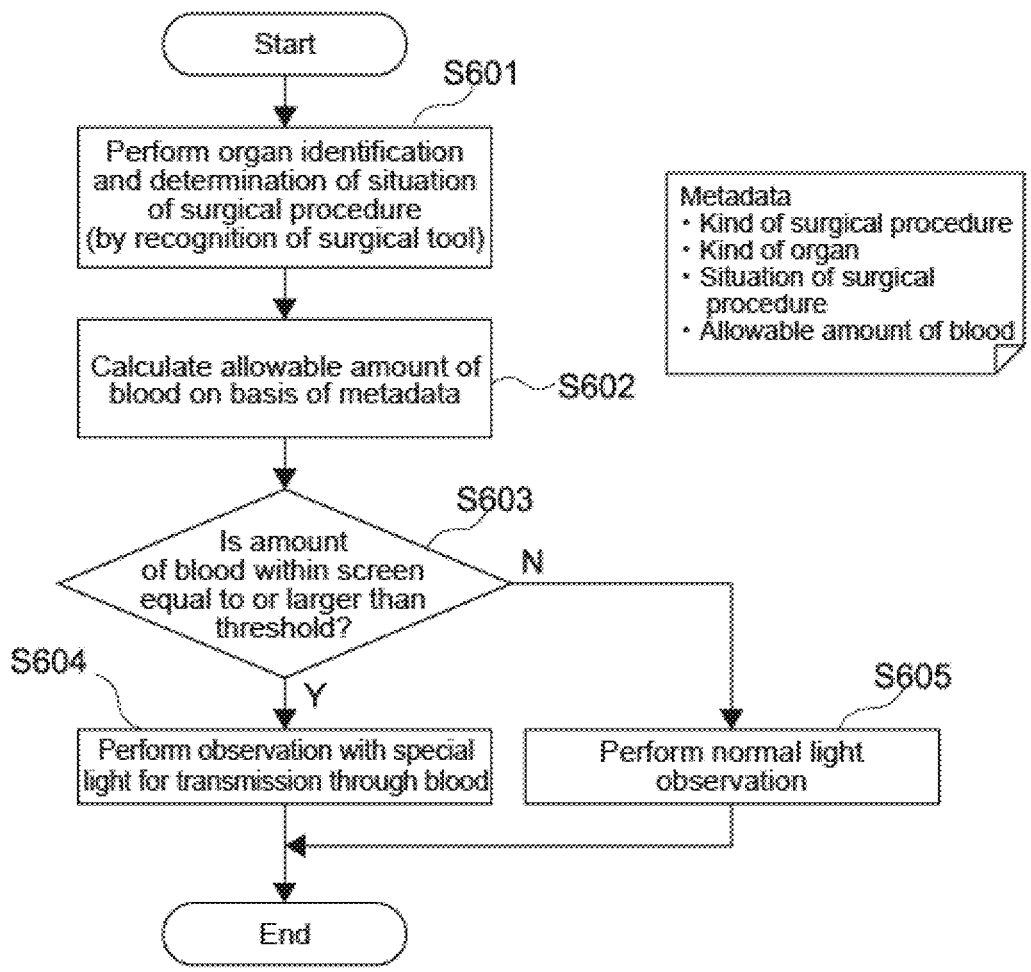
FIG. 21 A view depicting an information processing method in an assistance system according to an eighth embodiment.

FIG. 21 is a diagram depicting an information processing method associated with calculation of the metadata. FIG. 22 is a diagram depicting images of a surgical part before and after image processing in this embodiment.

The description will be made in accordance with the flow of FIG. 21.

The control unit 5063 causes the object recognition image processing unit 130 to extract characteristics from the first image picked up by the image pickup unit 5009 and to perform image recognition. With this configuration, the organ is determined by surgical tool recognition and the situation of the surgical procedure and the like are determined (S601).

The control unit 5063 calculates an amount of blood on the basis of the image recognition result. Further, the control unit 5063 calculates the metadata similar to the image recognition result on the basis of the database 110 of metadata and calculates an allowable amount of blood (S602). The kind of surgical procedure, the kind of organ, the situation of the surgical procedure, the allowable amount of blood, and the like are used as the metadata.

The control unit 5063 compares the amount of blood calculated on the basis of the image recognition result of the first image with the allowable amount of blood calculated in S602 and determines whether or not the amount of blood is equal to or higher than the threshold, i.e., it is larger than the allowable amount of blood (S603).

If determining Yes in S603, the control unit 5063 performs control such that the irradiation light becomes the special light for transmission through blood (S604). On the other hand, if determining No in S603, the control unit 5063 performs control such that the irradiation light becomes the normal light (S605).

In this embodiment, the parameter of the camera control to change the irradiation light into the special light for transmission through blood is made to correspond to the metadata of the situation where the amount of blood is larger than the allowable amount of blood. On the other hand, the parameter of the camera control to change the irradiation light into the normal light is made to correspond to the metadata of the situation where the amount of blood is equal to or smaller than the allowable amount of blood.

FIG. 22(*a*) is a first image picked up under irradiation with the normal light by the image pickup unit 5009 and FIG. 22(*b*) shows a second image picked up under irradiation with the special light for transmission through blood. In FIG. 22, the reference signs 7013 indicates blood and the reference signs 7014 indicates a tissue. Although the tissue 7014 has been hidden by the blood 7013 in an invisible state in the normal light observation as depicted in FIG. 22, the second image in which the blood 7013 is removed and the tissue 7014 can be identified is provided in the observation with the special light for transmission through blood. As described above, the image in which the tissue is emphasized can be obtained by switching to image pickup with special light for transmission through blood, and the surgery is more suitably performed.

Infrared (IR) light can be used for the special light for transmission through blood. The IR light may be constantly used or light according to a frame sequential method using the IR light and white light which is normal light may be used.

Ninth Embodiment

The description will be made with reference to FIGS. 23 to 25 by exemplifying endoscopic surgery of the stomach cancer. In a case of performing lymphadenectomy in fat sticking to a stomach wall during stomach cancer surgery, it may be difficult to recognize the boundary between the stomach wall and the fat and the stomach wall may be damaged which causes bleeding during the process of separating the fat. In this embodiment, in a case of a situation where the occupation percentage of the fat within the image is exceeds a certain value, assistance to cause display to be performed such that the boundary between the stomach wall and the fat becomes easy to be recognized is performed.

Figure 23:
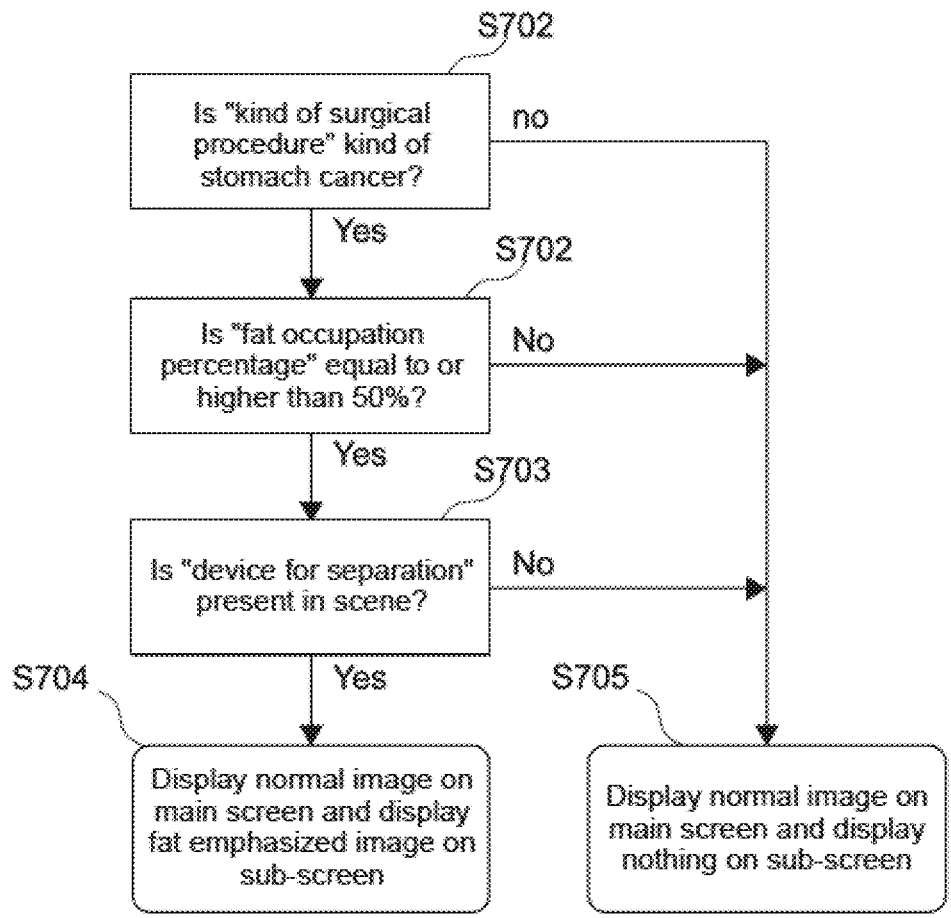
FIG. 23 A view depicting an information processing method in an assistance system according to a ninth embodiment.

FIG. 23 is a flowchart depicting an information processing method associated with calculation of the metadata. FIG. 24 is a diagram for describing fat emphasis processing calculation. FIG. 25 is a diagram depicting a screen displayed on the display apparatus 5041 in this embodiment.

The control unit 5063 causes the object recognition image processing unit 130 to extract characteristics from the first image picked up by the image pickup unit 5009 and to perform image recognition.

The control unit 5063 calculates the metadata similar to the image recognition result on the basis of the database 110 of metadata. The kind of surgical procedure, the occupation percentage of the fat, the presence and absence of the surgical tool, and the like are used as the metadata. The fat occupation percentage indicates the percentage of a region in the image, which is determined as the fat on the basis of the hue and structure information in the image and the like. The presence and absence of the surgical tool are stored as the metadata indicating whether or not a device for separation such as a dissector is present within the image, and for example, it indicates 1 in a case where it is present and it indicates 0 in a case where it is absence.

Hereinafter, the description will be made with reference to FIG. 23 by exemplifying the calculation of the metadata.

Here, the kind of surgical procedure is the stomach cancer, the fat occupation percentage is equal to or higher than 50%, and the parameter of the image quality adjustment of displaying the image subjected to the fat emphasis processing on the sub-screen is made to correspond to the metadata indicating that the device for separation as the surgical tool is present in the image. On the other hand, if at least one of the conditions that the kind of surgical procedure is a kind of stomach cancer, the fat occupation percentage is equal to or higher than 50%, and the device for separation as the surgical tool is present within the image, is not satisfied, a parameter to display the first image on the main screen and display nothing on the sub-screen is made to correspond to it.

As depicted in FIG. 23, the control unit 5063 determines whether or not the kind of surgical procedure is a kind of stomach cancer (S701). If determining Yes in S701, the processing proceeds to S702. If determining No in S701, the processing proceeds to S705, and control to display the first image on the main screen and to display nothing on the sub-screen is performed.

In S702, the control unit 5063 determines whether or not the fat occupation percentage is equal to or higher than 50%. If determining Yes in S702, the processing proceeds to S703. If determining No in S702, the processing proceeds to S705, control to display the first image on the main screen and to display nothing on the sub-screen is performed. It should be noted that the numerical value of the fat occupation percentage of 50% is an example and the assistant can set an arbitrary numerical value at the time of generation of the database of the metadata.

In S703, the control unit 5063 determines whether or not the device for separation is present within the image. If determining Yes in S703, control to display the first image on the main screen and to display an image subjected to fat emphasis processing on the sub-screen is performed (S704). If determining No in S703, the processing proceeds to S705, control to display the first image on the main screen and to display nothing on the sub-screen is performed.

Figure 25:
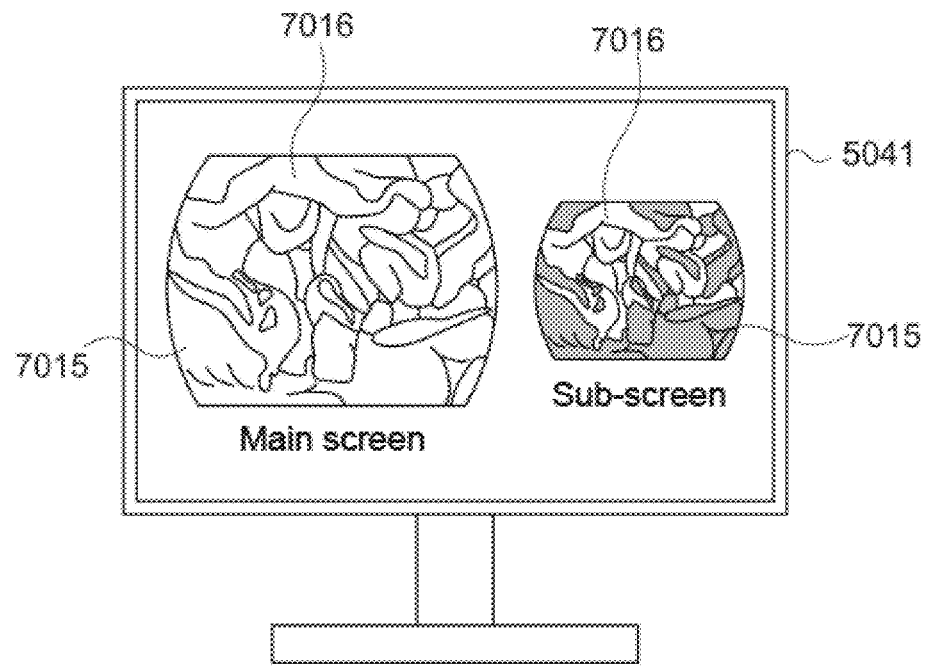
FIG. 25 A view depicting an example of a screen displayed on a display apparatus of the assistance system according to the ninth embodiment.

FIG. 25 is a diagram depicting a state in which the first image is displayed on the main screen and the second image in which the fat emphasis processing is performed is displayed on the sub-screen in the display apparatus 5041. In the first image before the fat emphasis processing, fat 7015 as a first tissue is displayed in yellow and a flesh tissue other than fat 7016 as a second tissue is displayed in red.

In contrast, in the second image subjected to fat emphasis processing, the fat 7015 is displayed in green and the flesh tissue other than the fat 7016 is displayed in pink. An image in which the boundary between the flesh tissue other than the fat 7016 and the fat 7015 is made clear by fat emphasis processing is provided. With this configuration, the danger that the flesh tissue other than the fat 7016 may be erroneously damaged during the fat separation process can be lowered.

By using the metadata of the fat occupation percentage as described above, the second image can be obtained by performing fat emphasis processing on the first image in a case where the fat occupies most of the surgical field and the tissue is embedded in the fat.

The fat emphasis processing is performed by extending the hue of all the living body colors using the hue near the fat as the center, for example. The colors of the living body are distributed in a range of yellow color to red color to purplish-red color and are extended near the second quadrant in the YCbCr space as depicted in FIG. 24. By performing processing of extending this color distribution in a hue direction, the color difference between the fat and the flesh tissue other than it is also extended and image quality processing to provide an image in which the fat portion is emphasized as a result is performed. The processing of extending such a color difference can be performed in accordance with a well-known method.

The emphasis processing will be described.

Figure 24:
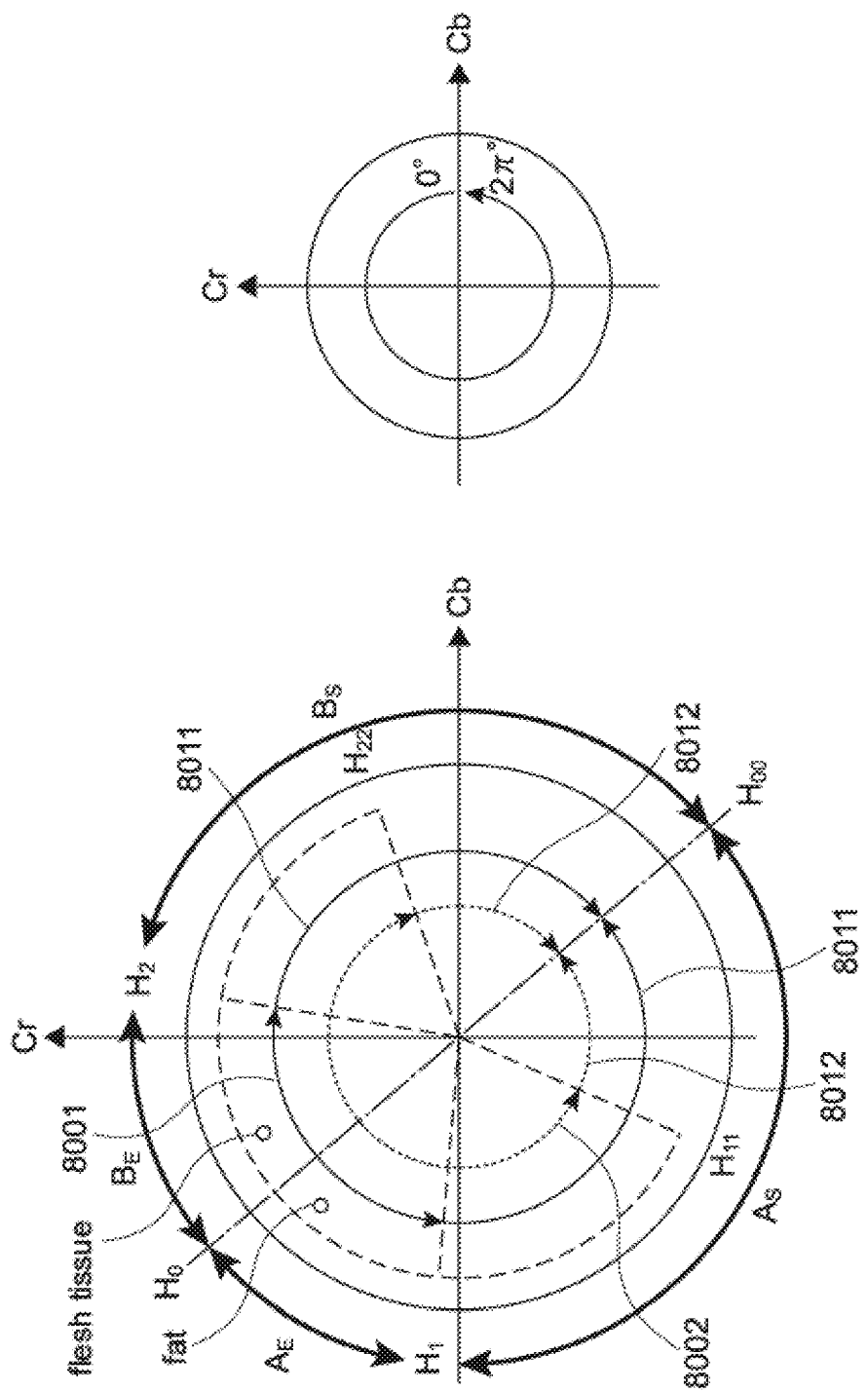
FIG. 24 A view depicting an example of fat emphasis processing calculation in the assistance system according to the ninth embodiment.

In FIG. 24, $H_1$ denotes a maximum living body hue, $H_2$ denotes a minimum living body hue, and living body colors are distributed within a range of $H_1$ to $H_2$. When the color signal values RGB of the flesh tissue 7016 and the fat 7015 are converted into values indicating the luminance, the hue, and color saturation components, the hue of the flesh tissue 7016 and the fat 7015 in the first image is positioned within a range of $H_1$ to $H_2$ (near the second quadrant).

Here, in FIG. 24, it is assumed that processing of extending the hue such that $H_1$ becomes $H_{11}$ and $H_2$ becomes $H_{22}$ is performed. It is assumed that the hue (near center hue) not to be moved even when extending processing is performed within the hue range to be extended is $H_0$. On the other hand, it is assumed that the hue not to be moved even when size reduction processing is performed is $H_{00}$ within the hue range to be reduced in size which is outside the hue range to be extended. In the figure, a range $A_E$ and a range $B_E$ are ranges to be subjected to extending processing and the range AS and the range $B_S$ are ranges to be subjected to size reduction processing. In the figure, a solid-line bent two-way arrow 8001 denotes a range to be subjected to extending processing. A dotted-line bent two-way arrow 8002 denotes a range as a result of extending processing. A solid-line arrow 8011 denotes a range to be subjected to size reduction processing. A dotted-line arrow 8012 denotes a range as a result of size reduction processing.

By performing such emphasis processing of extending the hue, a second image in which the hue of the flesh tissue other than the fat 7016 and the fat 7015 is changed and the fat is displayed in an emphasized state can be obtained. Here, the color space defined by the YCbCr values is used as the space for defining the luminance, the color saturation, and the hue, though not limited thereto. For example, YIQ, HVS, LCH, and the like which are other color space values may be used or Lab, Lch, XYZ, and the like other than the RGB may be used also for the color space which is a base.

It should be noted that in this embodiment, the occupation percentage of the first tissue within the first image is used as the metadata by exemplifying the fat as the first tissue, though the first tissue is not limited to the fat. Other tissues may be used. In this case, the numerical value of the occupation percentage of the first tissue suitable for the situation and the kind of first tissue is set as the metadata. It can also be applied to the vein, the artery, and the like, for example, other than the fat.

Figure 26:
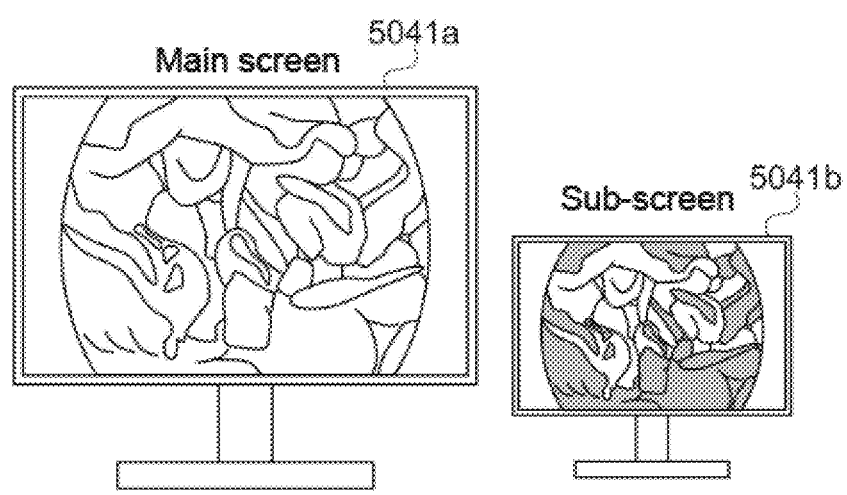
FIG. 26 An example depicting another display example of the screen displayed on the display apparatus in each embodiment.
Figure 27:
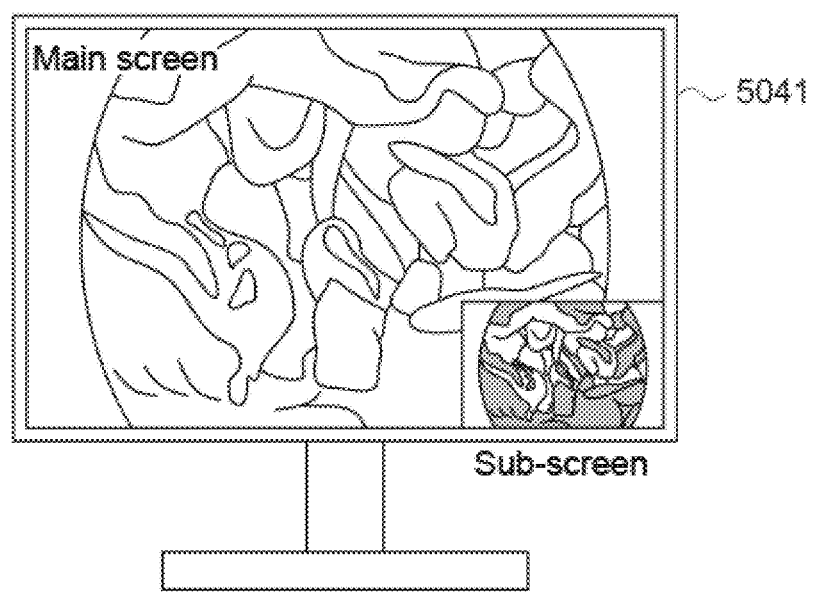
FIG. 27 An example depicting still another display example of the screen displayed on the display apparatus in each embodiment.

In the above-mentioned embodiment, the first image is displayed on the main screen and the second image is displayed on the sub-screen in the single display apparatus 5041, though not limited thereto. As depicted in FIG. 26, two display apparatuses 5041a and 5041b may be prepared, the one display apparatus 5041a may be caused to display the first image, and the other display apparatus 5041b may be caused to display the second image Further, as depicted in FIG. 27, the single display apparatus 5041 may be used and the sub-screen may be displayed overlapping a part of the main screen.

It should be noted that the present technology may also take the following configurations.

(1) An information processing apparatus, including a control unit that extracts, on the basis of a first image obtained by picking up an image of a surgical part including an affected part and metadata of a situation obtained from past surgery or examination, a parameter of assistance performed with respect to the situation, which is made to correspond to the metadata.

(2) The information processing apparatus according to (1), in which the control unit calculates the metadata similar to an image recognition result of the first image and extracts the parameter made to correspond to the calculated metadata.

(3) The information processing apparatus according to (1) or (2), in which
the control unit changes an image pickup condition of the surgical part on the basis of the extracted parameter.
(4) The information processing apparatus according to (3), in which
the control unit changes the image pickup condition by changing irradiation light with which the surgical part is to be irradiated, on the basis of the extracted parameter.
(5) The information processing apparatus according to (3), in which
the control unit changes the image pickup condition by adjusting a scale and a focal point at a time of image pickup on the basis of the extracted parameter.
(6) The information processing apparatus according to any of (3) to (5), in which
the control unit causes a display apparatus to display a second image obtained by changing the image pickup condition on the basis of the extracted parameter and picking up an image of the surgical part.
(7) The information processing apparatus according to (1) or (2), in which
the control unit causes a display apparatus to display a second image whose image quality is adjusted by causing the first image to be subjected to image processing on the basis of the extracted parameter.
(8) The information processing apparatus according to (7), in which
the surgical part includes a first tissue and a second tissue, and
the control unit causes the display apparatus to display the second image whose image quality is adjusted by causing the first image to be subjected to image processing such that a hue difference between the first tissue and the second tissue in the first image on the basis of the extracted parameter.
(9) The information processing apparatus according to (1) or (2), in which
the control unit causes a display apparatus to display a past image or video to be a reference on the basis of the extracted parameter.
(10) The information processing apparatus according to (1) or (2), in which
the control unit extracts, if determining that the first image has a situation of low visibility on the basis of the first image and the metadata, the parameter to cause the display apparatus to display an image picked up before the low visibility is caused.
(11) The information processing apparatus according to (1) or (2), in which
the control unit causes assistance information to be reported on the basis of the extracted parameter.
(12) An assistance system, including:
a database of metadata in which metadata of a situation obtained from past surgery or examination is stored;
a database of a parameter in which a parameter of assistance performed with respect to the situation made to correspond to the metadata is stored; and
a control unit that calculates, on the basis of the database of the metadata, metadata similar to an image recognition result of a first image obtained by picking up an image of a surgical part including an affected part and extracts the parameter made to correspond to the calculated metadata.
(13) An information processing method, including:
acquiring an image recognition result of a first image obtained by picking up an image of a surgical part including an affected part;
calculating metadata similar to the image recognition result of the first image from a database of metadata in which metadata of a situation obtained from past surgery or examination is stored; and
extracting a parameter of assistance performed with respect to the situation, which is made to correspond to the calculated metadata.

REFERENCE SIGNS LIST

100 assistance system
110 database of metadata
120 database of parameter
5039 CCU (information processing apparatus)
5041 display apparatus
5063 control unit
7001, 7002, 7003, 7004, 7005, 7012 affected part
7006 video in past dangerous event (past image or video to be reference)
7007 low-visibility image (first image)
7008 second image
7015 fat (first tissue)
7016 flesh tissue other than fat (second tissue)

The invention claimed is:

1. An information processing apparatus, comprising:
a memory that stores metadata of a plurality of situations obtained from past surgery or examination and a plurality of parameters of assistance corresponding to a plurality of assistances performed with respect to the plurality of the situations respectively in the past surgery or the examination, each of the plurality of the parameters of assistance corresponding to each of the metadata of each situation of the plurality of the situations; and
processing circuitry configured to
perform an image recognition of a first image obtained by picking up an image of a surgical part including an affected part to obtain an image recognition result;
calculate first metadata similar to the image recognition result of the first image;
extract, from among the plurality of the parameters stored in the memory, a first parameter of assistance that corresponds with the calculated first metadata the, first parameter of assistance corresponding to at least one of a scale and a focal point at a time of image pickup that was used in the past surgery or the examination; and
change an image pickup condition of the surgical part by adjusting the at least one of the scale and the focal point at the time of image pickup based on the extracted parameter.

2. The information processing apparatus according to claim 1, wherein
the processing circuitry changes the image pickup condition by changing irradiation light with which the surgical part is to be irradiated, based on the extracted parameter.

3. The information processing apparatus according to claim 1, wherein
the processing circuitry causes a display apparatus to display a second image obtained by changing the image pickup condition based on the extracted parameter and picking up an image of the surgical part.

4. The information processing apparatus according to claim 1, wherein
the processing circuitry causes a display apparatus to display a second image whose image quality is adjusted by causing the first image to be subjected to image processing based on the extracted parameter.

5. The information processing apparatus according to claim 4, wherein the surgical part includes a first tissue and a second tissue; and the processing circuitry causes the display apparatus to display the second image whose image quality is adjusted by causing the first image to be subjected to image processing such that a hue difference between the first tissue and the second tissue in the first image based on the extracted parameter.

6. The information processing apparatus according to claim 1, wherein the processing circuitry causes a display apparatus to display a past image or video to be a reference based on the extracted parameter.

7. The information processing apparatus according to claim 1, wherein the processing circuitry extracts, in response to determining that the first image has a situation of low visibility where a visibility of the first image is lower than a predetermined threshold based on the first image and the metadata, the parameter to cause the display apparatus to display an image picked up before the low visibility is caused.

8. The information processing apparatus according to claim 1, wherein the processing circuitry causes assistance information to be reported based on the extracted parameter.

9. The information processing apparatus according to claim 1, wherein the processing circuitry is configured to change the image pickup condition of the surgical part by adjusting the scale at the time of image pickup based on the extracted parameter.

10. The information processing apparatus according to claim 1, wherein the processing circuitry is configured to change the image pickup condition of the surgical part by adjusting the focal point at the time of image pickup based on the extracted parameter.

11. An information processing method, comprising:

storing, in a memory, metadata of a plurality of situations obtained from past surgery or examination and a plurality of parameters of assistance corresponding to a plurality of assistances performed with respect to the plurality of the situations respectively in the past surgery or the examination, each of the plurality of the parameters of assistance corresponding to each of the metadata of each situation of the plurality of the situations;

performing an image recognition of a first image obtained by picking up an image of a surgical part including an affected part to obtain an image recognition result;

calculating first metadata similar to the image recognition result of the first image;

calculating, using processing circuitry, first metadata similar to the image recognition result of the first image;

extracting, from among the plurality of the parameters stored in the memory, a first parameter of assistance that corresponds with the calculated first metadata the first parameter of assistance corresponding to at least one of a scale and a focal point at a time of image pickup that was used in the past surgery or the examination; and changing an image pickup condition of the surgical part by adjusting the at least one of the scale and the focal point at the time of image pickup based on the extracted parameter.

* * * * *